US008609607B2

(12) United States Patent
Moss et al.

(10) Patent No.: US 8,609,607 B2
(45) Date of Patent: Dec. 17, 2013

(54) MODIFIED DEFENSINS AND THEIR USE

(75) Inventors: Joel Moss, Bethesda, MD (US); Rodney L. Levine, Rockville, MD (US); Akihiro Wada, Nagasaki (JP); Toshiya Hirayama, Nagasaki (JP); Gregorino Paone, Rome (IT)

(73) Assignee: The United States of America as represented by the Secretary of the Department of Health and Human Services, Washington, DC (US)

( * ) Notice: Subject to any disclaimer, the term of this patent is extended or adjusted under 35 U.S.C. 154(b) by 0 days.

(21) Appl. No.: 13/344,509

(22) Filed: Jan. 5, 2012

(65) Prior Publication Data
US 2012/0107336 A1 May 3, 2012

Related U.S. Application Data

(60) Division of application No. 12/388,427, filed on Feb. 18, 2009, now Pat. No. 8,106,006, which is a continuation of application No. 10/504,838, filed as application No. PCT/US03/04649 on Feb. 18, 2003, now Pat. No. 7,511,015.

(60) Provisional application No. 60/358,504, filed on Feb. 19, 2002.

(51) Int. Cl.
*A61K 38/00* (2006.01)
*A61K 38/16* (2006.01)
*A61K 38/19* (2006.01)
*C07K 5/00* (2006.01)

(52) U.S. Cl.
USPC ........... 514/2.3; 514/21.3; 424/85.1; 435/375

(58) Field of Classification Search
None
See application file for complete search history.

(56) References Cited

U.S. PATENT DOCUMENTS

| | | |
|---|---|---|
| 5,386,021 A | 1/1995 | Moss et al. |
| 5,514,600 A | 5/1996 | Moss et al. |
| 5,716,816 A | 2/1998 | Moss et al. |
| 5,830,860 A | 11/1998 | Gray et al. |
| 5,834,310 A | 11/1998 | Moss et al. |
| 6,143,498 A | 11/2000 | Olsen et al. |
| 6,211,148 B1 | 4/2001 | Selsted et al. |
| 6,329,340 B1 | 12/2001 | Bougueleret et al. |
| 6,335,318 B1 | 1/2002 | Selsted et al. |
| 2005/0181446 A1 | 8/2005 | Roggen et al. |
| 2006/0074037 A1 | 4/2006 | Moss et al. |

FOREIGN PATENT DOCUMENTS

WO    WO 01/09175    2/2001

OTHER PUBLICATIONS

Pazgier et al., Curr. Pharm. Des., 2007, 13(30):3096-3118.*
DiNovo et al., Biochem., 2006, 45(14):4664-4673.*
Paone et al., J. Biol. Chem., 2006, vol. 281(25):17054-17060.*
Abedini et al., "A single-point mutation converts the highly amyloidogenic human islet amyloid polypeptide into a potent fibrillization inhibitor," *J. Am. Chem. Soc.*, 129(37):11300-11301, 2007.
Allport et al., "Reduction by inhibitors of mono(ADP-ribosyl)transferase of chemotaxis in human neutrophil leucocytes by inhibition of the assembly of filamentous actin," *Br. J. Clin. Pharmacol.* 118(5):1111-1118, 1996 (abstract only).
Allport et al., "A possible role for mono (ADP-ribosyl) transferase in the signalling pathway mediating neutrophil chemotaxis," *Br. J. Clin. Pharmacol.* 42(1):99-106, 1996 (abstract only).
Ayabe et al., "Activation of Paneth cell alpha-defensins in mouse small intestine," *J. Biol. Chem.* 277(7):5219-5228, 2002.
Bals, "Epithelial antimicrobial peptides in host defense against infection," *Respir. Res.*, 1:141-150, 2000.
Bauer et al., "Structure determination of human and murine beta-defensins reveals structural conservation in the absence of significant sequence similarity," *Protein Science*, 10:2470-2479, 2001.
Chang et al., "Identification of an enzymatic activity that hydrolyzes protein-bound ADP-ribose in skeletal muscle," *Biochem. Biophys. Res. Commun.*, 139(3):932-939, 1986.
Dinova et al., "ADP-Ribosylation of Cyclophilin a by *Pseudomonas aeruginosa* Exoenzymes S," *Biochemistry*, 45: 4664-4673, 2006.
Fehlbaum et al., "An essential amino acid induces epithelial beta-defensin expression," *PNAS* 97(23):12723-12728, 2000.
GenBank Accession No. AAC50382, Feb. 23, 1996, 1 page.
GenBank Accession No. CAA31952, Jul. 23, 1997, 1 page.
GenBank Accession No. NP_001916, Feb. 3, 2001, 2 pages.
GenBank Accession No. NP_001917, Feb. 3, 2001, 2 pages.
GenBank Accession No. NP_004075, Jan. 31, 2001, 3 pages.
GenBank Accession No. NP_066290, Feb. 3, 2001, 2 pages.
GenBank Accession No. P11479, Aug. 20, 2001, 3 pages.
Gera et al., "Human neutrophil peptide defensins induce single strand DNA breaks in target cells," *Cell Immunol.* 138(1):108-120, 1991 (abstract only).
Ishibashi et al., "Purification, cDNA cloning and modification of a defensin from the coconut rhinoceros beetle, Oryctes rhinoceros," *Eur. J. Biochem.* 266(2):616-623, 1999 (abstract only).

(Continued)

*Primary Examiner* — Xiaozhen Xie
(74) *Attorney, Agent, or Firm* — Klarquist Sparkman, LLP

(57) ABSTRACT

This disclosure provides modified antimicrobial agents, for example modified defensin polypeptides. Compositions including a modified arginine residue, such as an ADP-ribosylated and/or ribosylated alpha defensin polypeptide, are provided. Also provided are methods of modulating an immune response using the modified defensin polypeptides. Methods are provided for modulating an antimicrobial activity and for inhibiting a cytotoxic activity. Also disclosed are methods for treating diseases in a subject that are associated with an immune response, such as inflammatory and pulmonary diseases, using the disclosed modified defensin polypeptides.

10 Claims, 6 Drawing Sheets

(56) References Cited

OTHER PUBLICATIONS

Kharadia et al., "Effect of an arginine-specific ADP-ribosyltransferase inhibitor on differentiation of embryonic chick skeletal muscle cells in culture," *Exp. Cell Res.* 201(1):33-42, 1992 (abstract only).

Laing et al., "ADP-ribosylation of arginine," *Amino Acids*, pp. 1-13, Jul. 21, 2010.

Lehrer et al., "Human α-Defensins Inhibit Hemolysis Mediated by Cholesterol-Dependent Cytolysins," *Infection and Immunity*, 77(9): 4028-4040, 2009.

Lehrer et al., "Defensins of vertebrate animals," *Curr. Opin. Immunol.* 14(1):96-102, 2002.

Paone et al., "AD-ribosyltransferase-specific Modification of Human Neutrophil Peptide-1," *The Journal of Biological Chemistry*, 281(25): 17054-17060, 2006.

Paone et al., "ADP ribosylation of human neutrophil peptide-1 regulates its biological properties," *PNAS*, 99(12):8231-8235, 2002.

Pazgier et al., "Human Defensins: Synthesis and Structural Properties," *Current Pharmaceutical Design*, 13: 3096-3118, 2007.

Raj et al., "Large-scale synthesis and functional elements for the antimicrobial activity of defensinsBiochem," *J.* 347:633-641, 2000.

Risso, "Leukocyte antimicrobial peptides: multifunctional effector molecules of innate immunity," *J. of Leukocyte Biol.* 68:785-792, Dec. 2000.

Tang et al., "Defensins and host defense," *Science* 286(5439):420-421, 1999 (abstract only).

Tran et al., "Homodimeric theta-defensins from rhesus macaque leukocytes: isolation, synthesis, antimicrobial activities, and bacterial binding properties of the cyclic peptides," *J. Biol. Chem.* 277(5):3079-3084, 2002.

Wang et al., "Regulation of cytotoxic T cells by ecto-nicotinamide adenine dinucleotide (NAD) correlates with cell surface GPI-anchored/arginine ADP-ribosyltransferase," *J. Immunol.* 153(9):4048-4058, 1994 (abstract only).

Zolkiewska et al., "Integrin alpha 7 as substrate for a glycosylphosphatidylinositol-anchored ADP-ribosyltransferase on the surface of skeletal muscle cells," *J. Biol. Chem.* 268(34):25273-25276, 1993.

\* cited by examiner

```
                        SEQUENCE LISTING

<160> NUMBER OF SEQ ID NOS: 14

<210> SEQ ID NO 1
<211> LENGTH: 94
<212> TYPE: PRT
<213> ORGANISM: Homo sapien

<400> SEQUENCE: 1

Met Arg Thr Leu Ala Ile Leu Ala Ala Ile Leu Leu Val Ala Leu Gln
1               5                   10                  15

Ala Gln Ala Glu Pro Leu Gln Ala Arg Ala Asp Glu Val Ala Ala Ala
            20                  25                  30

Pro Glu Gln Ile Ala Ala Asp Ile Pro Glu Val Val Val Ser Leu Ala
        35                  40                  45

Trp Asp Glu Ser Leu Ala Pro Lys His Pro Gly Ser Arg Lys Asn Met
    50                  55                  60

Asp Cys Tyr Cys Arg Ile Pro Ala Cys Ile Ala Gly Glu Arg Arg Tyr
65                  70                  75                  80

Gly Thr Cys Ile Tyr Gln Gly Arg Leu Trp Ala Phe Cys Cys
                85                  90

<210> SEQ ID NO 2
<211> LENGTH: 30
<212> TYPE: PRT
<213> ORGANISM: Homo sapien

<400> SEQUENCE: 2

Ala Cys Tyr Cys Arg Ile Pro Ala Cys Ile Ala Gly Glu Arg Arg Tyr
1               5                   10                  15

Gly Thr Cys Ile Tyr Gln Gly Arg Leu Trp Ala Phe Cys Cys
            20                  25                  30

<210> SEQ ID NO 3
<211> LENGTH: 29
<212> TYPE: PRT
<213> ORGANISM: Homo sapien

<400> SEQUENCE: 3

Cys Tyr Cys Arg Ile Pro Ala Cys Ile Ala Gly Glu Arg Arg Tyr Gly
1               5                   10                  15

Thr Cys Ile Tyr Gln Gly Arg Leu Trp Ala Phe Cys Cys
            20                  25

<210> SEQ ID NO 4
<211> LENGTH: 30
<212> TYPE: PRT
<213> ORGANISM: Homo sapien

<400> SEQUENCE: 4

Asp Cys Tyr Cys Arg Ile Pro Ala Cys Ile Ala Gly Glu Arg Arg Tyr
1               5                   10                  15
```

```
Gly Thr Cys Ile Tyr Gln Gly Arg Leu Trp Ala Phe Cys Cys
            20                  25                  30
```

<210> SEQ ID NO 5
<211> LENGTH: 96
<212> TYPE: PRT
<213> ORGANISM: Homo sapien

<400> SEQUENCE: 5

```
Met Arg Ile Ile Ala Leu Leu Ala Ala Ile Leu Leu Val Ala Leu Gln
1               5                   10                  15

Val Arg Ala Gly Pro Leu Gln Ala Arg Gly Asp Glu Ala Gly Gln Glu
            20                  25                  30

Gln Arg Gly Pro Glu Asp Gln Asp Ile Ser Ile Ser Phe Ala Trp Asp
        35                  40                  45

Lys Ser Ser Ala Leu Gln Val Ser Gly Ser Thr Arg Gly Met Val Cys
    50                  55                  60

Ser Cys Arg Leu Val Phe Cys Arg Arg Thr Glu Leu Arg Val Gly Asn
65                  70                  75                  80

Cys Leu Ile Gly Gly Val Ser Phe Thr Tyr Cys Cys Thr Arg Val Asp
                85                  90                  95
```

<210> SEQ ID NO 6
<211> LENGTH: 34
<212> TYPE: PRT
<213> ORGANISM: Homo sapien

<400> SEQUENCE: 6

```
Val Cys Ser Cys Arg Leu Val Phe Cys Arg Arg Thr Glu Leu Arg Val
1               5                   10                  15

Gly Asn Cys Leu Ile Gly Gly Val Ser Phe Thr Tyr Cys Cys Thr Arg
            20                  25                  30

Val Asp
```

<210> SEQ ID NO 7
<211> LENGTH: 94
<212> TYPE: PRT
<213> ORGANISM: Homo sapien

<400> SEQUENCE: 7

```
Met Arg Thr Ile Ala Ile Leu Ala Ala Ile Leu Leu Val Ala Leu Gln
1               5                   10                  15

Ala Gln Ala Glu Ser Leu Gln Glu Arg Ala Asp Glu Ala Thr Thr Gln
            20                  25                  30

Lys Gln Ser Gly Glu Asp Asn Gln Asp Leu Ala Ile Ser Phe Ala Gly
        35                  40                  45

Asn Gly Leu Ser Ala Leu Arg Thr Ser Gly Ser Gln Ala Arg Ala Thr
    50                  55                  60

Cys Tyr Cys Arg Thr Gly Arg Cys Ala Thr Arg Glu Ser Leu Ser Gly
65                  70                  75                  80

Val Cys Glu Ile Ser Gly Arg Leu Tyr Arg Leu Cys Cys Arg
                85                  90
```

<210> SEQ ID NO 8
<211> LENGTH: 32
<212> TYPE: PRT
<213> ORGANISM: Homo sapien

<400> SEQUENCE: 8

```
Ala Thr Cys Tyr Cys Arg Thr Gly Arg Cys Ala Thr Arg Glu Ser Leu
```

```
                 1               5                  10                 15
Ser Gly Val Cys Glu Ile Ser Gly Arg Leu Tyr Arg Leu Cys Cys Arg
                20                 25                 30

<210> SEQ ID NO 9
<211> LENGTH: 100
<212> TYPE: PRT
<213> ORGANISM: Homo sapien

<400> SEQUENCE: 9

Met Arg Thr Leu Thr Ile Leu Thr Ala Val Leu Leu Val Ala Leu Gln
1               5                  10                 15

Ala Lys Ala Glu Pro Leu Gln Ala Glu Asp Asp Pro Leu Gln Ala Lys
                20                 25                 30

Ala Tyr Glu Ala Asp Ala Gln Glu Gln Arg Gly Ala Asn Asp Gln Asp
            35                 40                 45

Phe Ala Val Ser Phe Ala Glu Asp Ala Ser Ser Ser Leu Arg Ala Leu
    50                 55                 60

Gly Ser Thr Arg Ala Phe Thr Cys His Cys Arg Arg Ser Cys Tyr Ser
65                 70                 75                 80

Thr Glu Tyr Ser Tyr Gly Thr Cys Thr Val Met Gly Ile Asn His Arg
                85                 90                 95

Phe Cys Cys Leu
            100

<210> SEQ ID NO 10
<211> LENGTH: 30
<212> TYPE: PRT
<213> ORGANISM: Homo sapien

<400> SEQUENCE: 10

Thr Cys His Cys Arg Arg Ser Cys Tyr Ser Thr Glu Tyr Ser Tyr Gly
1               5                  10                 15

Thr Cys Thr Val Met Gly Ile Asn His Arg Phe Cys Cys Leu
                20                 25                 30

<210> SEQ ID NO 11
<211> LENGTH: 36
<212> TYPE: DNA
<213> ORGANISM: Artificial Sequence
<220> FEATURE:
<223> OTHER INFORMATION: ART-1 Forward Primer

<400> SEQUENCE: 11
acgtacaagc ttagccacct ggtgacacgt cgagac                            36

<210> SEQ ID NO 12
<211> LENGTH: 36
<212> TYPE: DNA
<213> ORGANISM: Artificial Sequence
<220> FEATURE:
<223> OTHER INFORMATION: ART-1 Reverse Primer

<400> SEQUENCE: 12
acgtacggta ccgtccaggt ggcagggcct agactt                            36

<210> SEQ ID NO 13
<211> LENGTH: 94
<212> TYPE: PRT
<213> ORGANISM: Homo sapien

<400> SEQUENCE: 13
```

```
Met Arg Thr Leu Thr Leu Leu Ser Ala Phe Leu Leu Val Ala Leu Gln
1               5                   10                  15

Ala Trp Ala Glu Pro Leu Gln Ala Arg Ala His Glu Met Pro Ala Gln
                20                  25                  30

Lys Gln Pro Pro Ala Asp Asp Gln Asp Val Val Ile Tyr Phe Ser Gly
            35                  40                  45

Asp Asp Ser Cys Ser Leu Gln Val Pro Gly Ser Thr Lys Gly Leu Ile
        50                  55                  60

Cys His Cys Arg Val Leu Tyr Cys Ile Phe Gly Glu His Leu Gly Gly
65                  70                      75                  80

Thr Cys Phe Ile Leu Gly Glu Arg Tyr Pro Ile Cys Cys Tyr
                85                  90

<210> SEQ ID NO 14
<211> LENGTH: 31
<212> TYPE: PRT
<213> ORGANISM: Homo sapien

<400> SEQUENCE: 14

Ile Cys His Cys Arg Val Leu Tyr Cys Ile Phe Gly Glu His Leu Gly
1               5                   10                  15

Gly Thr Cys Phe Ile Leu Gly Glu Arg Tyr Pro Ile Cys Cys Tyr
                20                  25                  30
```

MODIFIED DEFENSINS AND THEIR USE

CROSS-REFERENCE TO RELATED APPLICATIONS

This is a division of U.S. application Ser. No. 12/388,427, filed Feb. 18, 2009, now U.S. Pat. No. 8,106,006, issued Jan. 31, 2012, which is a continuation of U.S. application Ser. No. 10/504,838, which was filed Aug. 13, 2004, and met the requirements under 35 U.S.C. §371 (c)(1), (c)(2), and (c)(4) on Jun. 23, 2005, now U.S. Pat. No. 7,511,015, issued Mar. 31, 2009, which is the §371 U.S. National Stage of International Application No. PCT/US03/04649, filed Feb. 18, 2003, which was published in English under PCT Article 21(2), which in turn claims the benefit of U.S. Provisional Application No. 60/358,504, filed Feb. 19, 2002, all of which are incorporated by reference herein in their entirety.

INCORPORATION-BY-REFERENCE OF MATERIAL SUBMITTED AS AN ASCII TEXT FILE

A Sequence Listing is submitted herewith as an ASCII compliant text file named "Sequence_Listing.txt", created on Dec. 29, 2011, and having a size of 7.38 kilobytes, as permitted under 37 CFR 1.821(c). The material in the aforementioned file is hereby incorporated by reference in its entirety.

FIELD

The present disclosure relates generally to antimicrobial agents, such as defensins, and, more specifically, to a modified defensins such as adenosine-diphosphate (ADP)-ribosylated defensins and their use in modulating an immune response.

BACKGROUND

Defensins are small, cationic peptides containing six conserved cysteine residues that form three disulfide bonds. Functional, mature defensins arise by the sequential post-translational processing of prepro-proteins that are 93-95 amino acids in length. Mature alpha-defensins generally contain 29-33 residues, whereas mature beta-defensins are more basic and are generally between 34-37 amino acids in length. The recently identified theta defensins are formed by the head-to-tail ligation of two alpha defensin-related nonapeptides, generating a circular 18-residue polypeptide.

Defensins were first identified in neutrophils and have been detected in human, rabbit, guinea pig, and rat phagocytes. Four human alpha defensins have been isolated from neutrophils: human neutrophil peptide (HNP)-1, HNP-2, HNP-3, and HNP-4. HNP-1, HNP-2, and HNP-3 are stored in the azurophilic granules of neutrophils and constitute approximately 99% of the defensin content of the neutrophils. HNP-4 is also present in these granules, but at a concentration that is equivalent to only one percent of the other HNP polypeptides. Alpha defensins also include two human enteric defensins, human defensin (HD)-5 and HD-6, which are highly expressed in epithelial cells of the small intestine, specifically in the Paneth cells.

Defensins play important roles in the innate immune defense in vertebrates. Defensins are broad-spectrum antimicrobial molecules that are released from azurophilic granules into a phagosome for the nonoxidative killing of phagocytized infectious agents such as Gram-negative bacteria, Gram-positive bacteria, fungi, and certain enveloped viruses, by forming pores in their membranes. Constitutively expressed defensins contribute to an antimicrobial barrier at the epithelial cell surface and inducible epithelial defensins are highly expressed at areas of inflammation or infection. Thus, defensins play an important role in the body's natural immunity against infections. Defensins also play a role in the body's natural immunity against tumor cells.

The ubiquitous use of antibiotics has resulted in the selection of bacteria that are relatively resistant to these drugs. Furthermore, few drugs are effective against viral and fungal microorganisms. Thus, there is a continuing need to identify novel agents that reduce or inhibit the growth of such microorganisms as well as novel agents that may recruit inflammatory cells to enhance an immune response. Defensins exhibit a wide range of antimicrobial activities, including cytotoxicity towards bacterial cells, however these proteins are also cytotoxic for mammalian cells, including human epithelial and endothelial cells. This side effect may limit their usefulness as antimicrobial agents. Thus, there also exists a need to identify new methods of modifying existing agents, such as defensins, in order to modify their cytotoxic activity and give them superior antimicrobial activities.

SUMMARY

The disclosure provides a composition including a modified defensin polypeptide. In one embodiment, an arginine residue of the defensin polypeptide is modified by ADP-ribosylation or ribosylation to form an ADP-ribosylated or ribosylated defensin. In one embodiment, the defensin polypeptide is an alpha defensin. In another embodiment, the alpha defensin polypeptide is human neutrophil peptide-1. In one embodiment, the ADP-ribosylated or ribosylated defensin has antimicrobial activity less than that of unmodified defensin. In another embodiment, a pharmaceutical composition is provided that includes a modified defensin polypeptide.

Also provided herein is a substantially purified modified defensin polypeptide, or a functional fragment of the polypeptide, wherein the defensin or functional fragment is a cationic, arginine-rich polypeptide that has an antimicrobial activity. In one embodiment, the defensin polypeptide, or a functional fragment of the peptide, has at least one arginine residue that is ribosylated or ADP-ribosylated. In another embodiment, the defensin peptide, or a functional fragment of the peptide has antimicrobial activity.

The disclosure also provides a method for increasing an antimicrobial activity of a defensin polypeptide. Examples of these methods include ribosylating or ADP-ribosylating at least one arginine residue of the defensin polypeptide in order to increase the antimicrobial activity of the defensin polypeptide.

Also provided herein is a method of modulating an immune response against a microbe in a subject. The method includes administering to the subject a therapeutically effective amount of a modified defensin polypeptide. In one embodiment, the defensin polypeptide has an ADP-ribosylated or ribosylated arginine residue.

Also disclosed is a method of inhibiting a cytotoxic activity of a non-ADP-ribosylated or a non-ribosylated defensin polypeptide in a subject. In one embodiment, the method includes administering to the subject a therapeutically effective amount of an ADP-ribosylated or a ribosylated defensin in order to inhibit a cytotoxic activity of the non-ADP-ribosylated or non-ribosylated defensin.

A method is also disclosed for treating a subject who has a pulmonary disease. The method includes administering to the subject a therapeutically effective amount of a modified defensin polypeptide in order to treat the pulmonary disease. In one embodiment, an arginine residue in the defensin polypeptide is modified by ADP-ribosylation or ribosylation.

Also provided herein is a method for screening for an agent that affects ADP-ribosylation or ribosylation of a defensin. The method includes contacting a cell that expresses an ADP-ribosyltransferase with the agent and the defensin polypeptide, and evaluating the ADP-ribosylation. The method also includes contacting a cell that expresses ADP-ribosyltransferase and pyrophosphatase/phosphatase with the agent and the defensin polypeptide, and evaluating the ribosylation of the defensin polypeptide.

The disclosure also provides a pharmaceutical composition comprising a therapeutically effective amount of a ribosylated antimicrobial agent or an ADP-ribosylated antimicrobial agent in a pharmaceutically acceptable carrier. Specific, non-limiting examples of an antimicrobial agent include a defensin polypeptide, such as an alpha defensin, for example human neutrophil peptide-1, or lysozyme.

The foregoing and other features and advantages will become more apparent from the following detailed description of several embodiments, which proceeds with reference to the accompanying figures.

BRIEF DESCRIPTION OF THE FIGURES

FIG. 1B is 750 units, for FIG. 1C is 650 units and for FIG. 1D is 250 units. ADP-ribosylated HNP-1 and HNP-1 are indicated by solid and open arrows, respectively. Absorbance spectra of ADP-ribosylated HNP-1 (solid line) and HNP-1 (dotted line) were obtained during elution using an inline array detector (inset).

FIG. 2A is a graph demonstrating the cytotoxic activity of ADP-ribosylated HNP-1 versus that of non-ADP-ribosylated HNP-1 in a radial diffusion assay. Antimicrobial activity is positively correlated with the diameter of a zone cleared of *E. coli* growth by the indicated concentration of HNP-1 (○) or ADP-ribosylated-HNP-1 (□), minus the diameter of the central well (3 mm). Data are means±½ range of values from 2 independent experiments. FIG. 2B is a graph demonstrating the cytotoxic activity of ADP-ribosylated HNP-1 versus that of non-ADP-ribosylated HNP-1 using a chromium release assay. Cytotoxicity is positively correlated with lysis of chromium ($^{51}$Cr)-labeled A549 cells during incubation with the indicated concentrations of HNP-1 (○), ADP-ribosylated HNP-1 (□), or synthetic HNP-1 (sHNP) (Δ). Cell lysis is measured by the amount of chromium released from the damaged or broken cells. Percent of lysis was calculated as (cpm$_{exp}$-cpm$_{spont}$)/(cpm$_{max}$-cpm$_{spont}$)×100. Data are means±standard error of the mean (SEM) of values from 4 independent experiments.

FIG. 3A is a graph demonstrating the effect of incubating HNP-1 (100 nM) with the indicated concentrations of ADP-ribosylated HNP-1 before it is added to *E. coli* in a radial diffusion assay. Difference in zone size (◆) was calculated as in FIG. 2A. Data are means±SEM of values from 3 independent experiments. FIG. 3B is a line graph demonstrating the effect of incubating HNP-1 with ADP-ribosylated HNP-1 before it is added to $^{51}$Cr-labeled A549 cells in a chromium release assay. HNP-1 (12 µM) was incubated with the indicated concentrations of ADP-ribosylated HNP-1. Percentage of cell lysis (◆) was determined, as in FIG. 2B. Cytotoxicity is positively correlated with lysis of $^{51}$Cr-labeled A549 cells. The cytotoxic effects of HNP-1 (○) or ADP-ribosylated HNP-1 (□) are also shown. Data are means±½ range of values from 2 independent experiments.

In FIG. 4C, CD3$^+$ cells were incubated with 0.025, 0.25, 2.5, or 25 nM of HNP-1 or ADP-ribosyl HNP-1. Migration medium with Macrophage Inflammatory Peptide (MIP)-1β (5 ng/ml) and migration medium alone, were used as positive and negative controls, respectively. Chemotaxis percentage was calculated as follows: (number of cells migrated to the lower chamber in the experimental conditions−number of cells migrated in the negative control)/(number of cells migrated in the positive control−number of cells migrated in negative control)×100. Data are shown as means±SEM of 4 separated experiments, each performed in duplicate.

FIG. 5A demonstrates the alignment of RP-HPLC chromatograms of ART-1-catalyzed ADP-ribosylation of HNP-1 (continuous line) and the bronchial lavage sample from a smoker (dotted line). Arrows indicate elution times of ADP-ribosylated HNP-1 (46.5 minutes) and HNP-1 (48.5 minutes). In FIG. 5B profile 1 has a peak with an elution time compatible with ADP-ribosylated HNP-1 (46.5 minutes) and shows a mass of 3,983 daltons when analyzed by MALDI mass spectroscopy, consistent with ADP-ribosylated HNP-1. Incubation of ADP-ribosylated HNP-1 with pyrophosphatase/phosphatase produced ribosyl-HNP-1 (calculated 3,574 daltons) (profile 2) and incubation of ADP-ribosylated HNP-1 with ADP-ribosylarginine hydrolase cleaved the ribose-arginine linkage to release HNP-1 (calculated 3,443 daltons) (profile 3). The x axis represents mass to charge ratio (m/z).

SEQUENCE LISTING

Figure 1:
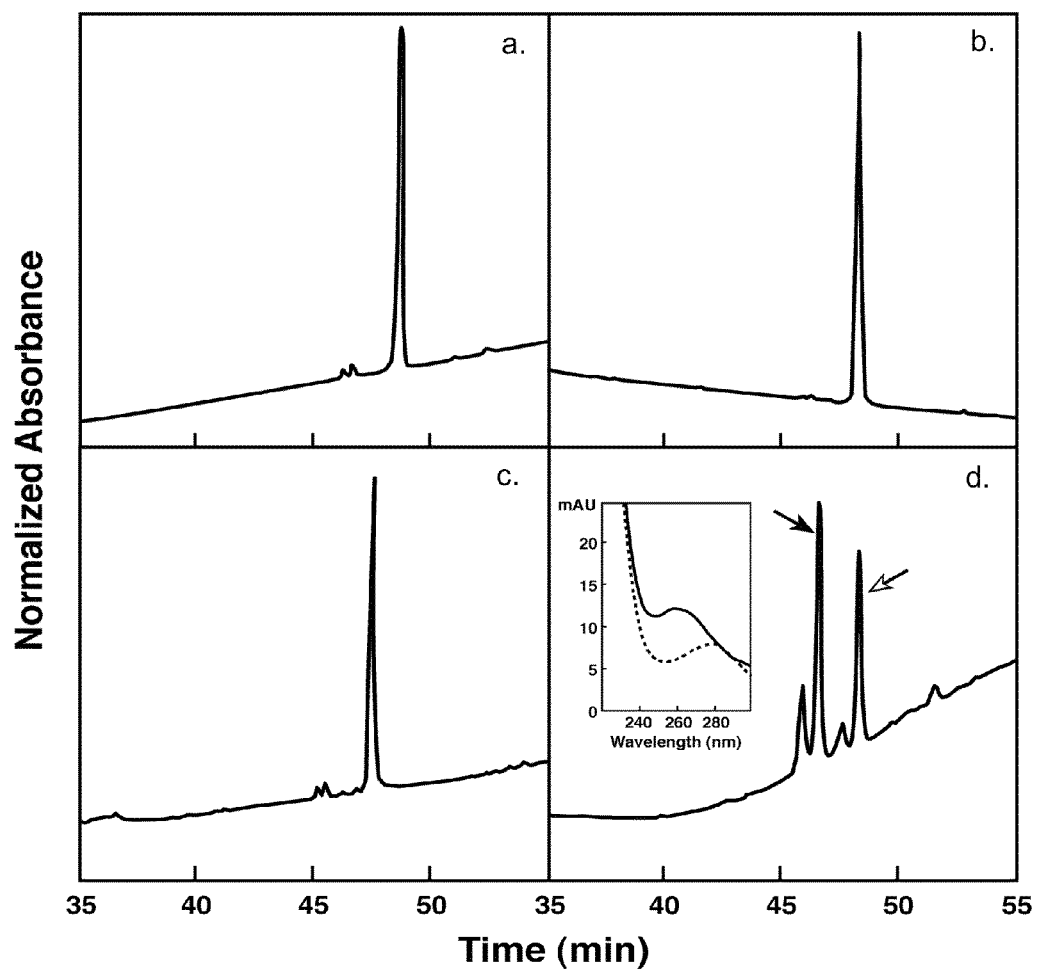
FIG. 1 is a series of reverse-phase high-performance liquid chromatography (RP-HPLC) elution profiles that demonstrate the separation of the products generated by ADP-ribosyltransferase (ART)-1-catalyzed ADP-ribosylation of HNP-1. HNP-1 was incubated with reaction buffer alone (FIG. 1A), nicotinamide adenine dinucleotide (NAD$^+$) (FIG. 1B), ART-1 (FIG. 1C), or ART-1 plus NAD$^+$ (FIG. 1D) and then analyzed by RP-HPLC. Absorbance at 210 nm, is shown as a function of elution time. Full scale for FIG. 1A

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. In the accompanying sequence listing:

SEQ ID NO:1 is the amino acid sequence of the HNP-1, HNP-2, HNP-3 prepro-protein.

SEQ ID NO:2 is the amino acid sequence of HNP-1.

SEQ ID NO:3 is the amino acid sequence of HNP-2.

SEQ ID NO:4 is the amino acid sequence of HNP-3.

SEQ ID NO:5 is the amino acid sequence of the HNP-4 prepro-protein.

SEQ ID NO:6 is the amino acid sequence of HNP-4.

SEQ ID NO:7 is the amino acid sequence of the HD-5 prepro-protein.

SEQ ID NO:8 is the amino acid sequence of HD-5.

SEQ ID NO:9 is the amino acid sequence of the HD-6 prepro-protein.

SEQ ID NO:10 is the amino acid sequence of HD-6.

SEQ ID NO:11 is the forward primer for mono-ADP-ribosyltransferase (ART)-1.

SEQ ID NO:12 is the reverse primer for ART-1.

SEQ ID NO:13 is the amino acid sequence of the Def-X prepro-protein SEQ ID NO:14 is the amino acid sequence of Def-X.

DETAILED DESCRIPTION

I. Abbreviations

| ADP | adenosine-diphosphate |
|---|---|
| ART | ADP-ribosyltransferase |
| ELISA | enzyme-linked immunosorbent assay |
| exp | experimental conditions |
| GPI | glycosylphosphatidylinositol |
| HD | human defensin |
| HNP | human neutrophil peptide |
| IL | interleukin |
| MALDI-MS | Matrix Assisted Laser Desorption Ionization-Time of Flight-Mass Spectrometry |
| MIP-1β | macrophage inflammatory protein-1β |
| max | maximal release |
| NAD | nicotinamide adenine dinucleotide |
| RP-HPLC | reverse-phase high-performance liquid chromatography |
| SEM | standard error of the mean |
| spont | spontaneous release |

II. Terms

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the invention, the following explanations of specific terms are provided:

ADP-ribosylation: Reaction in which ADP-ribose is covalently attached to another compound. A family of eukaryotic and prokaryotic mono-ADP-ribosyltransferases (ARTs) catalyze the transfer of ADP-ribose from nicotinamide adenine dinucleotide (NAD) to the guanidino group of arginine residues on proteins. Bacterial products (e.g., cholera toxin, pertussis toxin, diphtheria toxin) are included among the ARTs.

A family of mammalian ADP-ribosyltransferases that are secreted or localized on the cell surface through glycosylphosphatidylinositol (GPI) anchors are expressed preferentially on epithelial and inflammatory cells such as lymphocytes and neutrophils. Substrates of the five known mammalian ADP-ribosyltransferases (ART-1, ART-2, ART-3, ART-4, ART-5) include proteins that are involved in critical cellular events (e.g., lymphocyte activation, neutrophil chemotaxis). Two of these transferases, ART-1 and ART-5, specifically modify arginine residues in proteins.

As disclosed herein, a number of proteins used in host defense are basic and arginine-rich and thus could serve as acceptors for ADP-ribose. These include, but may not be limited to, alpha defensins (HNP-1, HNP-2, HNP-3, HNP-4, HD-5, HD-6); beta defensins (hBD1, hBD-2, hBD-3, hBD-4); Major Basic Protein; Eosinophil Cationic Protein; Human Cathelicin LL-37 (hCAP18) and lysozyme.

Adult respiratory distress syndrome (ARDS): Sudden pulmonary interstitial and alveolar edema, which usually develops within a few days after an initiating trauma. ARDS is thought to result from alveolar injury that has led to increased capillary permeability. Also called acute respiratory distress syndrome.

Animal: Living multi-cellular vertebrate organisms, a category that includes, for example, mammals and birds. The term mammal includes both human and non-human mammals. Similarly, the term "subject" includes both human and veterinary subjects.

Antimicrobial agent: A substance, including, but not limited to, a chemical compound, small molecule, peptide mimetic, peptide, or protein for killing microorganisms or suppressing their multiplication or growth. Specific, non-limiting examples of agents with antimicrobial activity include, but are not limited to, defensins, lysozyme, myeloperoxidase, and bacterial/permeability-increasing protein (BPI). An agent has "antimicrobial activity" if it can damage a microorganism in such a way that it results in the death of a microorganism or suppresses the growth of a microorganism. An antimicrobial activity includes, but may not be limited to, cell lysis due to cytotoxicity. Antimicrobial activity can result from T cell chemotaxis or neutrophil recruitment. In one embodiment, an antimicrobial activity is the lysis of a bacterial cell.

Arginine: An amino acid ($C_6H_{14}N_4O_2$) found in plants and animals that is essential for the human diet; also produced by the breakdown of proteins. Also encompassed are functional analogues of arginine, and structurally modified arginine molecules (e.g., agmatine).

Asthma: A disorder of the respiratory system characterized by inflammation, narrowing of the airways and increased reactivity of the airways to inhaled agents. Asthma is frequently, although not exclusively, associated with atopic or allergic symptoms.

Bacterial/Permeability-Increasing Protein (BPI): Cationic protein present in the azurophilic granules of polymorphonuclear leukocytes (PMN). BPI is toxic only toward Gram-negative bacteria. This specificity is attributable to the strong attraction of BPI for the lipopolysaccharides in the bacterial envelope.

B cell or B lymphocyte: One of the two major types of lymphocytes. The antigen receptor on B lymphocytes, sometimes called the B cell receptor, is a cell-surface immunoglobulin. On activation by an antigen, B cells differentiate into cells producing antibody molecules of the same antigen-specificity as this receptor.

cDNA (complementary DNA): A piece of DNA lacking internal, non-coding segments (introns) and regulatory sequences that determine transcription. cDNA is synthesized in the laboratory by reverse transcription from messenger RNA extracted from cells.

Chronic Bronchitis: An inflammation of the lining of the bronchial tubes. When the bronchi are inflamed and/or infected, less air is able to flow to and from the lungs and a heavy mucus or phlegm is coughed up, resulting in bronchitis. A brief attack of acute bronchitis with cough and mucus production can occur with severe colds. Chronic bronchitis is characterized by the presence of a mucus-producing cough most days of the month, three months of a year for two successive years without other underlying disease to explain the cough. It may precede or accompany pulmonary emphysema. Cigarette smoking is by far the most common cause of chronic bronchitis. The bronchial tubes of people with chronic bronchitis may also have been irritated initially by bacterial or viral infections. Air pollution and industrial dusts and fumes are also causes. Once the bronchial tubes have been irritated over a long period of time, excessive mucus is produced constantly, the lining of the bronchial tubes becomes thickened, an irritating cough develops, air flow may be hampered, and the lungs are endangered. The bronchial tubes then make an ideal breeding place for infectious agents.

Crohn's Disease: An Inflammatory Bowel Disease, the general name for diseases that cause inflammation in the intestines. Crohn's Disease causes inflammation in the small intestine. Crohn's Disease usually occurs in the lower part of the small intestine (ileum) but it can affect any part of the digestive tract, from the mouth to the anus. The inflammation extends deep into the lining of the affected organ. The inflammation can cause pain and can make the intestines empty frequently, resulting in diarrhea. Crohn's Disease may also be called ileitis or enteritis.

Chronic Obstructive Pulmonary Disease (COPD): Includes emphysema and chronic bronchitis—diseases that are characterized by obstruction to air flow. Emphysema and chronic bronchitis frequently coexist. It does not include other obstructive diseases such as asthma.

Cystic fibrosis: A recessive genetic disease in which the exocrine glands of afflicted individuals produce abnormally thick mucus which block the intestines and lung passageways and produce scarring and lesions in the lungs and pancreas.

Cytokines: Proteins made by cells that affect the behavior of other cells, such as lymphocytes and neutrophils. In one embodiment, a cytokine is a chemokine, a molecule that affects cellular trafficking. Cytokines include, but may not be limited to, MIP-$\beta$, IL-1, IL-8, IL-10, granulocyte-macrophage colony stimulating factor (GMCSF), granulocyte colony stimulating factor (GCSF), neurokinin, and tumor necrosis factor-alpha (TNF-$\alpha$).

Defensins: Small, cationic peptides that have six conserved cysteine residues that form three disulfide bonds. Functional defensins arise by the sequential post-translational processing of a prepro-protein of 93-95 amino acids in length. The members of the defensin family are divided into different classes. The alpha-defensins generally contain 29-33 residues. The beta-defensins are more basic than alpha defensins and are generally between 34-37 amino acids in length (Raj et al., *Biochem J.;* 347:633-41, 2000). The recently identified theta defensins are formed by the head-to-tail linkage of two alpha defensin-related nonapeptides, generating a circular 18-residue polypeptide (Tang et al., *Science;* 286:498-502, 1999).

Defensins were first identified in neutrophils and have been detected in human, rabbit, guinea pig, and rat phagocytes. Alpha defensins include, but are not be limited to, HNP-1, HNP-2, HNP-3, HNP-4, human defensin (HD)-5, and HD-6. Alpha defensins also include the recently identified HNP-4 homolog, defensin (Def)-X (see U.S. Pat. No. 6,329,340 herein incorporated by reference). HNP-1, HNP-2, and HNP-3 are products of the same gene (GenBank Accession No. P11479 herein incorporated by reference). HNP-4 is the product of a different gene (GenBank Accession No. NP_001916 herein incorporated by reference). HD-5 (GenBank Accession No. NP_066290) and HD-6, (GenBank Accession No. NP_001917 herein incorporated by reference) are two human enteric defensins.

Defensins are toxic for a variety of infectious agents, such as Gram-negative bacteria, Gram-positive bacteria, fungi, and certain enveloped viruses. Defensins act by forming pores in membranes of the infectious agent and generating voltage-dependent channels. Antimicrobial activities of defensins include, but are not limited to, lysis of bacteria, fungi, or viruses; toxicity for bacteria, fungi or viruses; leukocyte (e.g., T cell) chemotaxis; and leukocyte (e.g., neutrophil) recruitment. Without being bound by theory, defensins play an important role in the body's natural immunity against infections. Defensins are also cytotoxic for several normal and malignant cells. A "modified defensin" is a defensin that includes a modified arginine residue. An "unmodified defensin" is a defensin that includes any unmodified (native) arginine residue.

DNA: Deoxyribonucleic acid. DNA is a long chain polymer which constitutes the genetic material of most living organisms (some viruses have genes composed of ribonucleic acid (RNA)). The repeating units in DNA polymers are four different nucleotides, each of which contains one of the four bases, adenine, guanine, cytosine and thymine bound to a deoxyribose sugar to which a phosphate group is attached. Triplets of nucleotides (referred to as codons) code for each amino acid in a polypeptide. The term codon is also used for the corresponding (and complementary) sequence of three nucleotides in the mRNA that is transcribed from the DNA.

Emphysema: A condition in which there is over-inflation of structures in the lungs known as alveoli, or air sacs. This over-inflation results from a breakdown of the walls of the alveoli, which causes a decrease in respiratory function and often, breathlessness. Early symptoms of emphysema include shortness of breath and cough. Emphysema and chronic bronchitis together comprise chronic obstructive pulmonary disease (COPD).

Encode: A polynucleotide is said to "encode" a polypeptide if, in its native state or when manipulated by methods well known to those skilled in the art, it can be transcribed and/or translated to produce the mRNA for and/or the polypeptide or a fragment thereof. The anti-sense strand is the complement of such a nucleic acid, and the encoding sequence can be deduced therefrom.

Functionally Equivalent: Nucleic acid or polypeptide sequence alterations, for example in an ADP-ribosylated HNP-1 polypeptide, that do not alter a function of the nucleic acid or the polypeptide. In one embodiment, the function is the promotion of neutrophil recruitment. In another embodiment the function is cytotoxicity. Such sequence alterations can include, but are not limited to, substitutions, deletions, base modifications, mutations, labeling, and insertions.

Immune cell: Any cell involved in a host defense mechanism. These can include, for example, T cells, B cells, natural killer cells, neutrophils, mast cells, macrophages, antigen-presenting cells, basophils, eosinophils, and neutrophils.

Immune response: A response of a cell of the immune system, such as a neutrophil, a B cell, or a T cell, to a stimulus. In one embodiment, the immune response involves the phagocytosis of a microbe by a neutrophil, followed by the fusion of the neutrophil's azurophilic granules with the phagosome and/or the release of the contents of the neutrophil's azurophilic granules extracellularly. In another embodiment, the response is specific for a particular antigen (an "antigen-specific response").

Immune system deficiency: A disease or disorder in which the subject's immune system is not functioning normally, quantitatively or qualitatively, or in which it would be useful to boost a subject's immune response. In a non-limiting example, a subject with an immune system deficiency has a tumor (e.g., tumors of the brain, lung (e.g., small cell and non-small cell), ovary, breast, prostate, colon, as well as other carcinomas and sarcomas). In another non-limiting example, the subject has an immune system deficiency, such as an immunodeficiency disease resulting from a human immunodeficiency virus (HIV) infection.

Infectious agent: An agent that can infect a subject and/or cause an infection, including, but not limited to, viruses, bacteria, and fungi.

Examples of infectious virus include: Retroviridae (for example, human immunodeficiency viruses, such as HIV-1 (also referred to as HTLV-III, LAV or HTLV-III/LAV, or HIV-III; Paramyxoviridae (for example, parainfluenza viruses, mumps virus, measles virus, respiratory syncytial virus); Orthomyxoviridae (for example, influenza viruses); and Herpesviridae (herpes simplex virus (HSV) 1 and HSV-2, varicella zoster virus, cytomegalovirus (CMV), herpes viruses).

Examples of infectious bacteria include: *Helicobacter pyloris, Borelia burgdorferi, Legionella pneumophilia, Mycobacteria* sps (such as. *M. tuberculosis, M. avium, M. intracellulare, M. kansaii, M. gordonae*), *Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus* (viridans group), *Streptococcus faecalis, Streptococcus bovis, Streptococcus* (anaerobic sps.), *Streptococcus pneumoniae*, pathogenic *Campylobacter* sp., *Enterococcus* sp., *Haemophilus influenzae, Bacillus antracis, corynebacterium diphtheriae, corynebacterium* sp., *Erysipelothrix rhusiopathiae, Clostridium perfringers, Clostridium tetani, Enterobacter aerogenes, Klebsiella pneumoniae, Pasturella multocida, Bacteroides* sp., *Fusobacterium nucleatum, Streptobacillus moniliformis, Treponema pallidium, Treponema pertenue, Leptospira*, and *Actinomyces israelii*.

Examples of infectious fungi include, but are not limited to, *Cryptococcus neoformans, Histoplasma capsulatum, Coccidioides immitis, Blastomyces dermatitidis, Chlamydia trachomatis, Candida albicans*.

Other infectious organisms (such as protists) include: *Plasmodium falciparum* and *Toxoplasma gondii*.

Inflammation: A generalized response by the body as a result of tissue damage. The tissue damage can be due to trauma, lack of blood supply, hemorrhage, autoimmunity, transplanted exogenous tissue, or infection. Inflammation includes the release of many components of the immune system (e.g., defensins, IL-1 and tumor necrosis factor), attraction of cells to the site of the damage, swelling of tissue due to the release of fluid, and other processes.

During the inflammatory processes, a variety of soluble factors are involved in the recruitment of cells involved in the inflammatory response through increased expression of cellular adhesion molecules and chemoattraction. Many of these soluble factors regulate the activation of both the resident cells (such as fibroblasts, endothelial cells, tissue macrophages, and mast cells) and the newly recruited inflammatory cells (such as monocytes, lymphocytes, neutrophils, and eosinophils). In one embodiment, activated neutrophils release azurophilic granules that contain defensins. High defensin levels can be found in airway secretions of patients with inflammatory lung diseases.

Inflammatory Bowel Disease: Two separate diseases (Crohn's Disease and Ulcerative Colitis) that cause inflammation of the bowel and can cause arthritis or inflammation in joints. Crohn's Disease involves inflammation of the colon or small intestines. Ulcerative Colitis is characterized by ulcers and inflammation of the lining of the colon. The amount of the bowel disease usually influences the severity of arthritis symptoms.

Innate Immunity: Provides the first line of defense against many common microorganisms and is essential for the control of common bacterial infections. Includes antimicrobial peptides (e.g., defensins), epithelial barriers, phagocytic cells (neutrophils, macrophages), natural killer (NK) cells, the complement system, and cytokines that regulate and coordinate many of the activities of these cells. Defensins are present at the surface of epithelial cells, such as those lining the gut and the lungs, and in microbicidal organelles (e.g., azurophilic granules) of the phagocytic cells of the hematopoietic system (e.g., neutrophils and macrophages) and therefore are an important component to the innate immune system. Innate immunity can be supplemented by the administration of a modified defensin polypeptide. In one embodiment, an ADP-ribosylated HNP-1 polypeptide, or otherwise modified defensin, is administered to a subject. In another embodiment, a ribosyl-HNP-1 polypeptide is administered to a subject.

Isolated: A biological component (such as a nucleic acid, peptide or protein) that has been substantially separated, produced apart from, or purified away from other biological components in the cell of the organism in which the component naturally occurs, i.e., other chromosomal and extrachromosomal DNA and RNA, and proteins. Nucleic acids, peptides and proteins that have been "isolated" thus include nucleic acids and proteins purified by standard purification methods. The term also embraces nucleic acids, peptides and proteins prepared by recombinant expression in a host cell, as well as chemically synthesized nucleic acids and proteins.

Leukocyte: Cells in the blood, also termed "white cells," that are involved in defending the body against infective organisms and foreign substances. Leukocytes are produced in the bone marrow. There are five main types of white blood cells, subdivided between two main groups: polymorphonuclear leukocytes (neutrophils, eosinophils, basophils) and mononuclear leukocytes (monocytes and lymphocytes). When an infection is present, the production of leukocytes increases or leukocytes may be recruited to the site of infection.

Lymphocytes: A type of white blood cell that is involved in the immune defense of the body. There are two main types of lymphocytes: B-cells and T-cells.

Lysozyme: A highly basic 14.6 kDa protein (isoelectric point 11.1) of 129 amino acids and containing 4 disulfide bonds. Lysozyme is a glycosidase that hydrolyzes the bond between N-acteylmuramic acid and N-acetylglucosamine, thus cleaving an important polymer of the cell wall of many bacteria. Lysozyme is present in tears, saliva and in the lysosomes of phagocytic cells. It is an important antibacterial defense, particularly against Gram-positive bacteria.

Mammal: This term includes both human and non-human mammals. Similarly, the term "subject" includes both human and veterinary subjects.

Microorganism: An organism that can be seen only through a microscope. Microorganisms include bacteria, protozoa, algae, and fungi. Viruses are also classified as microorganisms. A microorganism is also known as a microbe.

Modified Arginine Residue: Any modification of an arginine in a protein. In one embodiment, the modification takes place on the guanidino group of the arginine residue. Modification of the guanidino group includes but is not limited to, the modification of an arginine residue by ADP-ribosylation, acylation, alkylation, or polymer conjugation. An arginine residue that is ADP ribosylated can be further modified for example, by the pyrophosphatase/phosphatase cleavage of a pyrophosphate to yield a ribosyl-arginine residue. In one embodiment, a decarboxylated arginine residue is a modified arginine residue known as agmatine ($C_5H_{14}N_4$).

Modulator: An agent that quantitatively or qualitatively modulates the activity of a protein as measured by the change in an experimental parameter. A modulator can be essentially any compound, such as a polypeptide, a hormone, a nucleic acid, a sugar, a lipid and the like.

Myeloperoxidase: A peroxidase found in the lysosomal granules of leukocytes, particularly macrophages and neutrophils. Myeloperoxidase is an oxidoreductase that catalyzes the reaction of hydrogen peroxide and halide ions to produce cytotoxic acids (such as hypochlorous acid) and other intermediates; these play a role in oxygen-dependent killing of microorganisms and tumor cells.

Natural killer (NK) cell: These are large, usually granular, non-T, non-B lymphocytes, which kill certain tumor cells. NK cells are important in innate immunity to viruses and other intracellular pathogens, as well as in antibody-dependent cell-mediated cytotoxicity.

Nucleic acid: A deoxyribonucleotide or ribonucleotide polymer in either single or double-stranded form, and unless otherwise limited, encompasses known analogues of natural nucleotides that hybridize to nucleic acids in a manner similar to naturally occurring nucleotides.

Neutrophil: Neutrophils are leukocytes of the Polymorphonuclear Leukocyte subgroup that are also known as granulocytes. Neutrophils contain a lobed nucleus and abundant cytoplasmic granules that stain with neutral dyes. Neutrophils form a primary defense against bacterial infection. Like all the cells of the immune system, neutrophils are produced in the bone marrow and circulate in the bloodstream. However, neutrophils move out of blood vessels into infected tissue in order to engulf and kill microorganisms (e.g., bacteria, fungus, virus). Neutrophils perform their function partially through the phagocytosis of other cells and foreign substances. Neutrophils are recruited to a site of infection by following a concentration gradient of chemoattractants or cytokines.

Oligonucleotide: A linear polynucleotide sequence of up to about 200 nucleotide bases in length, for example a polynucleotide (such as DNA or RNA) which is at least 6 nucleotides, for example at least 15, 50, 100 or even 200 nucleotides long.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

Pharmaceutical agent: A chemical compound or composition capable of inducing a desired therapeutic or prophylactic effect when properly administered to a subject or a cell. "Incubating" includes a sufficient amount of time for an agent to interact with a cell. "Contacting" includes incubating an agent in solid, or liquid, form with a cell.

A "therapeutically effective amount" is a quantity of a specific substance sufficient to achieve a desired effect in a subject being treated. For instance, this can be the amount necessary to inhibit viral, fungal, or bacterial replication or to measurably alter symptoms of the viral, fungal, or bacterial infection. When administered to a subject, a dosage will generally be used that will achieve target tissue concentrations (for example, in lymphocytes) that has been shown to achieve a desired in vitro effect.

Pharmaceutically acceptable carriers: The pharmaceutically acceptable carriers useful in this disclosure are conventional. *Remington's Pharmaceutical Sciences*, by E. W. Martin, Mack Publishing Co., Easton, Pa., $15^{th}$ Edition (1975), describes compositions and formulations suitable for pharmaceutical delivery of modified antimicrobial peptides, such as alpha defensins or lysozyme.

In general, the nature of the carrier will depend on the particular mode of administration employed. For instance, parenteral formulations usually comprise injectable fluids that include pharmaceutically and physiologically acceptable fluids such as water, physiological saline, balanced salt solutions, aqueous dextrose, glycerol, or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, pH buffering agents, or the like, for example sodium acetate or sorbitan monolaurate.

Pneumonia: An inflammation of the lungs caused by a bacterial, viral, or fungal infection Polynucleotide: A linear nucleotide sequence, including sequences of greater than 100 nucleotide bases in length.

Polypeptide: A polymer in which the monomers are amino acid residues that are joined together through amide bonds. When the amino acids are alpha-amino acids, either the L-optical isomer or the D-optical isomer can be used, the L-isomers being preferred in nature. The term polypeptide or protein as used herein encompasses any amino acid sequence and includes, but may not be limited to, modified sequences such as ADP-ribosylated proteins, ribosyl-proteins, and glycoproteins. The term polypeptide is specifically intended to cover naturally occurring proteins, as well as those that are recombinantly or synthetically produced.

Substantially purified polypeptide as used herein refers to a polypeptide that is substantially free of other proteins, lipids, carbohydrates or other materials with which it is naturally associated. In one embodiment, the polypeptide is at least 50%, for example at least 80%, free of other proteins, lipids, carbohydrates or other materials with which it is naturally associated. In another embodiment, the polypeptide is at least 90% free of other proteins, lipids, carbohydrates or other materials with which it is naturally associated. In yet another embodiment, the polypeptide is at least 95% free of other proteins, lipids, carbohydrates or other materials with which it is naturally associated.

Conservative amino acid substitution tables providing functionally similar amino acids are well known to one of ordinary skill in the art. The following six groups are examples of amino acids that are considered to be conservative substitutions for one another:

1) Alanine (A), Serine (S), Threonine (T);
2) Aspartic acid (D), Glutamic acid (E);

3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

Any cDNA sequence variant will preferably introduce no more than twenty, and preferably fewer than ten amino acid substitutions into the encoded polypeptide. Variant amino acid sequences may, for example, be 80%, 90%, 95% or even 98% identical to the native amino acid sequence. Programs and algorithms for determining percentage identity can be found at the NCBI website.

Preventing or treating a disease: Preventing a disease refers to inhibiting completely, or in part, the development or progression of a disease, for example in a person who is known to have a predisposition to a disease. An example of a person with a known predisposition is someone with a history of diabetes in the family, or who has been exposed to factors that predispose the subject to a condition, such as lupus or rheumatoid arthritis. Treating a disease refers to a therapeutic intervention that ameliorates at least one sign or symptom of a disease or pathological condition, or interferes with a pathophysiological process, after the disease or pathological condition has begun to develop.

Protein: A biological molecule encoded by a gene and comprised of amino acids.

Pulmonary disease: A disease of the respiratory system, including the lungs and bronchial tree. Pulmonary diseases include cystic fibrosis, emphysema, asthma, sarcoidosis, chronic bronchitis, pulmonary fibrosis, pneumonia, and adult respiratory distress syndrome.

Pulmonary fibrosis: Chronic inflammation and progressive fibrosis of alveolar walls, with steady, progressive shortness of breath, resulting in death from lack of oxygen or right heart failure.

Purified: The term purified does not require absolute purity; rather, it is intended as a relative term. Thus, for example, a purified peptide preparation is one in which the peptide or protein is more enriched than the peptide or protein is in its natural environment within a cell. Preferably, a preparation is purified such that the protein or peptide represents at least 50% of the total peptide or protein content of the preparation.

Pyrophosphatase: An enzyme that catalyzes the hydrolysis of pyrophosphate into two phosphate groups.

Recombinant: A recombinant nucleic acid is one that has a sequence that is not naturally occur or was made artificially. Artificial combination is often accomplished by chemical synthesis or, more commonly, by the artificial manipulation of isolated segments of nucleic acids, e.g., by genetic engineering techniques. Similarly, a recombinant protein is one encoded by a recombinant nucleic acid molecule.

Sarcoidosis: A disease of unknown cause in which inflammation, consisting of granulomas, occurs in lymph nodes, lungs, liver, eyes, skin, or other tissues. Tissue samples from involved organs show granulomas, which are clusters of macrophages, lymphocytes, and multinucleated giant cells. Possible causes of sarcoidosis include a hypersensitivity response, a genetic predisposition, infection, or chemicals.

Subject: Living multi-cellular vertebrate organisms, a category that includes both human and non-human mammals.

T Cell: A white blood cell critical to the immune response. T cells include, but are not limited to, CD4$^+$ T cells and CD8$^+$ T cells. A CD4$^+$ T lymphocyte is an immune cell that expresses a marker on its surface known as "cluster of differentiation 4" (CD4). These cells, also known as helper T cells, help orchestrate the immune response, including antibody responses and killer T cell responses. CD8$^+$ T cells express the "cluster of differentiation 8" (CD8) marker. In one embodiment, a CD8 T cell is a cytotoxic T lymphocyte. In another embodiment, a CD8 T cell is a suppressor T cell.

T cell chemotaxis: The directed locomotion of a T cell along a concentration gradient of chemotactically active factors, such as cytokines. Cells showing positive chemotaxis move towards areas with higher concentrations of these agents, those showing negative chemotaxis move away from these areas.

An increase in T cell chemotaxis includes, but may not be limited to, an increase in the distance or rate of T cell migration, an increase in the number of T cells migrating, an increase in the types of T cells migrating in a sample in response to a chemotactic stimulus, as compared to a control sample which does not receive the chemotactic stimulus.

Therapeutically effective dose: A dose sufficient to prevent advancement, or to cause regression of the disease, or which is capable of relieving symptoms caused by the disease, such as pain or swelling.

Treatment: Refers to both prophylactic inhibition of initial infection or disease, and therapeutic interventions to alter the natural course of an untreated infection or disease process, such as a tumor growth or an infection with a bacteria.

Ulcerative colitis: An Inflammatory Bowel Disease characterized by ulcers and inflammation of the lining of the colon.

Unless otherwise explained, all technical and scientific terms used herein have the same meaning as commonly understood by one of ordinary skill in the art to which this invention belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present invention, suitable methods and materials are described below. In case of conflict, the present specification, including explanations of terms, will control. In addition, the materials, methods, and examples are illustrative only and not intended to be limiting.

Modified Immunomodulatory Polypeptides

A composition is provided herein that is a polypeptide that modulates an immune response and that includes a modified arginine residue. In one embodiment, the polypeptide that modifies an immune response is an antimicrobial agent. A specific, non-limiting example of an antimicrobial agent is a defensin polypeptide, for example an alpha defensin.

In one specific embodiment, the alpha defensin is a vertebrate polypeptide. In another specific embodiment, the alpha defensin polypeptide is a mammalian polypeptide. In yet another specific embodiment, the alpha defensin polypeptide is from a human. In other embodiments, the alpha defensin polypeptide is from a monkey, a rabbit, a rat, a cat, a dog, a pig, a sheep, or a mouse. In a specific, non-limiting example, the alpha defensin is human neutrophil peptide (HNP)-1. In other specific, non-limiting examples, the alpha defensin polypeptide is HNP-2, HNP-3, HNP-4, HD-5, HD-6, or Def-X.

The alpha defensins include HNP-1, HNP-2, HNP-3, HNP-4, HD-5, HD-6, and Def-X. HNP-1, HNP-2, and HNP-3 are products of the same 94 amino acid prepro-protein. In one embodiment, this protein has the following sequence:

```
                (SEQ ID NO: 1, see also GenBank Accession No.
                    P11479, herein incorporated by reference)
MRTLAILAAILLVALQAQAEPLQARADEVAAAPEQIAADIPEVVVSLAW

DESLAPKHPGSRKNMDCYCRIPACIAGERRYGTCIYQGRLWAFCC;.
```

HNP-1 is one member of the family of alpha defensins produced by cleavage of the preproprotein. In one embodiment, HNP-1 has a sequence as set forth as:

```
                                        (SEQ ID NO: 2)
ACYCRIPACIAGERRYGTCIYQGRLWAFCC;.
```

HNP-2 is another member of the family of alpha defensins produced by cleavage of the preproprotein. In one embodiment, HNP-2 has a sequence as set forth as:

```
                                        (SEQ ID NO: 3)
CYCRIPACIAGERRYGTCIYQGRLWAFCC;.
```

HNP-3 is a third member of the family of alpha defensins produced by cleavage of the preproprotein. In one embodiment, HNP-3 has a sequence as set forth as:

```
                                        (SEQ ID NO: 4)
DCYCRIPACIAGERRYGTCIYQGRLWAFCC;.
```

HNP-4 is an alpha defensin that is the product of a preproprotein having a sequence as set forth as:

```
                (SEQ ID NO: 5, see also GenBank Accession No.
                    NP_001916, herein incorporated by reference)
MRIIALLAAILLVALQVRAGPLQARGDEAGQEQRGPEDQDISISFAWDKS

SALQVSGSTRGMVCSCRLVFCRRTELRVGNCLIGGVSFTYCCTRVD.
```

In one embodiment, HNP-4 has a sequence as set forth as:

```
                                        (SEQ ID NO: 6)
VCSCRLVFCRRTELRVGNCLIGGVSFTYCCTRVD;.
```

HD-5 is produced by cleavage of the following preproprotein having a sequence as set forth as:

```
            (SEQ ID NO: 7, GenBank Accession No. NP_066290,
                    herein incorporated by reference)
MRTIAILAAILLVALQAQAESLQERADEATTQKQSGEDNQDLAISFAGN

GLSALRTSGSQARATCYCRTGRCATRESLSGVCEISGRLYRLCCR;.
```

In one embodiment, HD-5 has a sequence as set forth as:

```
                                        (SEQ ID NO: 8)
ATCYCRTG RCATRESLSG VCEISGRLYR LCCR;.
```

HD-6 is produced by cleavage of the following preproprotein having a sequence as set forth as:

```
            (SEQ ID NO: 9, GenBank Accession No. NP_001917,
                    herein incorporated by reference)
MRTLTILTAVLLVALQAKAEPLQAEDDPLQAKAYEADAQEQRGANDQDF

AVSFAEDASSSLRALGSTRAFTCHCRRSCYSTEYSYGTCTVMGINHRFC

CL;.
```

In one embodiment, HD-6 has a sequence as set forth as:

```
                                        (SEQ ID NO: 10)
TCHCRRSCYS TEYSYGTCTV MGINHRFCCL;.
```

Def-X is produced by cleavage of the following preproprotein having a sequence as set forth as:

```
                (SEQ ID NO: 13, see U.S. Pat. No. 6,329,340,
                        herein incorporated by reference)
MRTLTLLSAFLLVALQAWAEPLQARAHEMPAQKQPPADDQDVVIYFSG

DDSCSLQVPGSTKGLICHCRVLYCIFGEHLGGTCFILGERYPICCY.
```

In one embodiment, Def-X has a sequence as set forth as:

```
                                        (SEQ ID NO: 14)
ICHCRVLYCIFGEHLGGTCFILGERYPICCY
```

As disclosed herein, a modified alpha defensin includes an arginine residue modified at the guanidino group. In one embodiment, the arginine residue is modified by ADP-ribosylation to form an ADP-ribosylated arginine residue. An alpha defensin including at least one ADP-ribosylated residue is referred to as an ADP-ribosylated defensin. In several embodiments, the ADP-ribosylated alpha defensin includes at least one, at least two, at least three, or at least four ADP-ribosylated arginine residues.

An ADP-ribose is covalently attached to another compound by ADP-ribosylation. Two mammalian ARTs, ART-1 and ART-5, are known to specifically modify arginine residues in proteins. In one embodiment, the ART substrate (the source of the ADP-ribose) is NAD.

ADP-ribose acceptors of the five known mammalian ARTs include basic and arginine-rich proteins that are involved in host defense (e.g., lymphocyte activation, neutrophil chemotaxis). ADP-ribose acceptors that contain an arginine can also be modified by an ART, but need not be arginine rich or basic. ADP-ribose acceptors include, but may not be limited to, alpha defensins (HNP-1, HNP-2, HNP-3, HNP-4, HD-5, HD-6, Def-X), beta defensins (hBD1, hBD-2, hBD-3, hBD-4), Major Basic Protein, Eosinophil Cationic Protein, Human Cathelicin LL-37 (hCAP18), and lysozyme. Thus, an ADP-ribosyltransferase can be used to produce ADP-ribosylated immunomodulatory polypeptides, such as a defensin.

In one specific, non-limiting example, the alpha defensin is HNP-1 and includes at least one ADP-ribosylated arginine residue. In another specific, non-limiting example, the alpha defensin is HNP-1 that is ADP-ribosylated on an arginine residue at position 14 of SEQ ID NO:2. In another embodiment, HNP-1 is ADP-ribosylated on an additional arginine residue and the ADP-HNP-1 includes at least one, at least two, at least three, or at least four ADP-ribosylated arginine residues.

In another embodiment, a pyrophosphate is cleaved in an ADP-ribosylated arginine, followed by the removal of phosphate, to yield a ribosyl-arginine. An alpha defensin including at least one ribosyl-arginine is referred to as a ribosylated alpha defensin. In one embodiment, a pyrophosphate linkage is cleaved by a pyrophosphatase/phosphatase and phosphate is removed from an ADP-ribosylated alpha defensin polypeptide. In another embodiment, the ribosylated alpha defensin is HNP-1. In other embodiments, the ribosylated alpha defensin is ribosylated-HNP-2, -HNP-3, -HNP-4, -HD-5, -HD-6, or -Def-X to yield ribosyl-HNP-2, -HNP-3, -HNP-4, -HD-5, -HD-6, -Def-X.

The modification of an arginine residue on its guanidino group also includes, but is not limited to, acylation, alkylation, or polymer conjugation. In one embodiment, a decarboxylated arginine residue is a modified arginine residue known as agmatine ($C_5H_{14}N_4$).

The defensin polypeptide can be modified by the addition of arginine residues to the polypeptide. In one embodiment, the at least one arginine is added to the amino terminal end of the polypeptide. In one specific, non-limiting example two arginines are added to the amino terminal end of the alpha defensin polypeptide. In another embodiment, at least one arginine is added to the carboxy terminal end of the polypeptide. In one specific, non-limiting example, two arginines are added to the carboxy terminal end of the polypeptide. In yet another embodiment, at least one arginine is added to both the amino and carboxy terminal ends of the polypeptide.

Antimicrobial agents, other than alpha defensins, are also encompassed by the disclosure. Examples of antimicrobial agents, other than alpha defensins, that are modified by ADP-ribosylation or ribosylation include, but are not limited to, lysozyme, BPI, beta defensins (hBD1, hBD-2, hBD-3, hBD-4), Major Basic Protein, Eosinophil Cationic Protein, Human Cathelicin LL-37 (hCAP18), and myeloperoxidase.

Pharmaceutical Compositions and Administration

Pharmaceutical compositions that include an ADP-ribosylated antimicrobial agent or a ribosyl-antimicrobial agent can be formulated with an appropriate solid or liquid carrier, depending upon the particular mode of administration chosen. A specific, non-limiting example of an ADP-ribosylated antimicrobial agent includes an ADP-ribosylated defensin polypeptide, for example an ADP-ribosylated alpha defensin. A specific, non-limiting example of a ribosylated antimicrobial agent includes a ribosylated defensin polypeptide, for example a ribosylated alpha defensin. The pharmaceutically acceptable carriers and excipients useful in this disclosure are conventional. For instance, parenteral formulations usually comprise injectable fluids that are pharmaceutically and physiologically acceptable fluid vehicles such as water, physiological saline, other balanced salt solutions, aqueous dextrose, glycerol or the like. Excipients that can be included are, for instance, other proteins, such as human serum albumin or plasma preparations. If desired, the pharmaceutical composition to be administered can also contain minor amounts of non-toxic auxiliary substances, such as wetting or emulsifying agents, preservatives, and pH buffering agents and the like, for example sodium acetate or sorbitan monolaurate.

Medicinal and pharmaceutical agents, for instance immunostimulants, also can be included. Immunostimulants include, but are not limited to, cytokines, such as Macrophage Inflammatory Protein (MIP)-β, IL-1, IL-8, IL-10, granulocyte-macrophage colony stimulating factor, granulocyte colony stimulating factor, neurokinin, and tumor necrosis factor-alpha, for example.

The dosage form of the pharmaceutical composition will be determined by the mode of administration chosen. For instance, in addition to injectable fluids, topical, inhalation, oral and suppository formulations can be employed. Topical preparations can include eye drops, ointments, sprays, patches and the like. Inhalation preparations can be liquid (e.g., solutions or suspensions) and include mists, sprays and the like. Oral formulations can be liquid (e.g., syrups, solutions or suspensions), or solid (e.g., powders, pills, tablets, or capsules). Suppository preparations can also be solid, gel, or in a suspension form. For solid compositions, conventional non-toxic solid carriers can include pharmaceutical grades of mannitol, lactose, starch, or magnesium stearate. Actual methods of preparing such dosage forms are known, or will be apparent, to those skilled in the art.

The pharmaceutical compositions that include an ADP-ribosylated defensin polypeptide, or ribosyl defensin molecule, can be formulated in unit dosage form, suitable for individual administration of precise dosages. In one specific, non-limiting example, a unit dosage can contain from about 1 ng to about 1 mg of ADP-ribosylated HNP-1 polypeptide. The amount of active compound(s) administered will be dependent on the subject being treated, the severity of the affliction, and the manner of administration, and is best left to the judgment of the prescribing clinician. Within these bounds, the formulation to be administered will contain a quantity of the active component(s) in amounts effective to achieve the desired effect in the subject being treated.

The compounds of this disclosure can be administered to humans or other animals on whose tissues they are effective in various manners such as topically, orally, intravenously, intramuscularly, intraperitoneally, intranasally, intradermally, intrathecally, subcutaneously, via inhalation or via suppository. The particular mode of administration and the dosage regimen will be selected by the attending clinician, taking into account the particulars of the case (e.g. the subject, the disease, the disease state involved, and whether the treatment is prophylactic). Treatment can involve daily or multi-daily doses of compound(s) over a period of a few days to months, or even years.

A therapeutically effective amount of a modified defensin polypeptide, such as an ADP-ribosylated alpha defensin polypeptide or a ribosyl-alpha defensin polypeptide, can be the amount of ADP-ribosylated alpha defensin polypeptide or ribosyl-alpha defensin polypeptide necessary to modulate the immune system of a subject. Specific immunostimulatory effects that can be caused by ADP-ribosylated alpha defensin polypeptide or ribosyl-alpha defensin polypeptide are described herein. In some embodiments, an immunomodulatory amount of an ADP-ribosylated defensin polypeptide or ribosyl-defensin polypeptide is an amount sufficient to stimulate an immune response for instance, increased T cell chemotaxis or promotion of neutrophil recruitment.

A therapeutically effective amount of modified defensin polypeptide, such as an ADP-ribosylated defensin polypeptide or ribosyl-defensin polypeptide, can be administered in a single dose, or in several doses, for example daily, during a course of treatment. However, the effective amount of ADP-ribosylated defensin polypeptide or ribosyl-defensin polypeptide will be dependent on the subject being treated, the severity and type of the affliction, and the manner of administration of the therapeutic(s).

Site-specific administration of the disclosed compounds can be used, for instance by applying the modified defensin polypeptide (for example a ribosyl-alpha defensin polypeptide) to a region of inflammation, a region of infection, or a region suspected of being prone to inflammation or infection.

Also encompassed by the present disclosure are pharmaceutical compositions that include ADP-ribosylated or ribosylated antimicrobial agents, other than alpha defensins, and a pharmaceutically acceptable carrier. Such pharmaceutical compositions include ADP-ribosylated or ribosylated antimicrobial agents such as lysozyme, BPI, beta defensins (hBD1, hBD-2, hBD-3, hBD-4), Major Basic Protein, Eosinophil Cationic Protein, Human Cathelicin LL-37 (hCAP18), and myeloperoxidase.

The present disclosure also includes combinations of a modified antimicrobial agent, such as an ADP-ribosylated alpha defensin polypeptide or ribosyl-alpha defensin polypeptide, with one or more other agents useful in the treatment of an immune-related disorder, condition, or disease. For example, the compounds of this disclosure can be administered in combination with effective doses of modified antimicrobial agents other than defensins, immuno stimulants, anti-tumor agents, anti-inflammatory agents, anti-infectives, and/or vaccines. The term "administration in combination" or "co-administration" refers to both concurrent and sequential administration of the active agents. A subject that is infected with an infectious agent, or displays an immune suppression, will be a candidate for treatment using the therapeutic methods disclosed herein, as described below.

Method of Modulating an Immune Response

A method is disclosed herein of modulating an immune response of an antimicrobial agent such as, for example, a defensin polypeptide or a lysozyme. Defensin polypeptides are antimicrobial peptides that are involved in the innate immune defense and are cytotoxic for microbes such as bacteria, fungi, and certain types of viruses. In addition, they stimulate IL-8 release from neighboring cells and induce an increase in T cell chemotaxis. As disclosed herein, the modification of an arginine residue in a defensin polypeptide can alter its antimicrobial activity and/or modify an immune response. Thus, a method is provided herein for modulating the anti-microbial activity of a defensin, such as an alpha defensin. In several embodiments, ADP-ribosylating a defensin or ribosylating a defensin increases the anti-microbial activity of the defensin. In several specific, non-limiting examples, the alpha defensin, includes but is not limited to, HNP-1, HNP-2, HNP-3, HNP-4. In specific, non-limiting examples, the modified alpha defensin is ADP-ribosylated HNP-1 or ribosylated HNP-1.

The antimicrobial activity can be antibacterial, antifungal, or antiviral activity. In one embodiment, an alteration in antimicrobial activity is a decrease in antimicrobial activity. In several non-limiting examples, the change in antimicrobial activity is at least about a 50% decrease, at least about a 75% decrease, at least about an 80% decrease, at least about a 90% decrease, at least about a 95% decrease, at least about a 98% decrease, or at least about a 100% decrease. In one embodiment, an alteration in antimicrobial activity is an increase in antimicrobial activity. In several specific, non-limiting examples, the change in antimicrobial activity is at least about a 50% increase, at least about a 75% increase, at least about an 80% increase, at least about a 90% increase, at least about a 95% increase, at least about a 98% increase, or at least about a 100% increase. In one embodiment, the altered antimicrobial activity is increased lysis of bacteria, fungi, or viruses.

In another embodiment, the altered antimicrobial activity is an increase in cytokine production. The increase in cytokine expression can be an increase in cytokine secretion, expression, and/or release. In one specific, non-limiting example, the cytokine is IL-8.

In yet another embodiment, the altered antimicrobial activity is an increase in the recruitment of inflammatory cells. In one specific, non-limiting example, the inflammatory cells are neutrophils. In a further embodiment, the altered antimicrobial activity is an increase in inflammatory cell chemotaxis. In one specific, non-limiting example the inflammatory cells are T cells.

In one embodiment, the antimicrobial activity is increased as compared to unmodified (native) alpha defensin polypeptide. In a further embodiment, the antimicrobial activity is decreased as compared to unmodified (native) alpha defensin polypeptide. In one specific, non-limiting example, the modified alpha defensin is an ADP-ribosylated HNP-1 polypeptide and the unmodified alpha defensin is non-ADP-ribosylated HNP-1 polypeptide. In another specific, non-limiting example, the modified alpha defensin is a ribosyl-HNP-1 polypeptide and the unmodified alpha defensin is non-ribosyl-HNP-1 polypeptide.

In one embodiment, a method of modifying an immune response against a microbe is provided. The method includes administering a therapeutically effective amount of a modified defensin to a subject infected with or at risk of being infected with the microbe, thereby modulating the immune response against the microbe. In one embodiment, modifying immune response includes decreasing cytotoxic activity. In another embodiment, modification of the immune response includes increasing neutrophil recruitment.

Neutrophil recruitment can be measured by any method known to one of skill in the art. In one embodiment, promotion of neutrophil recruitment is measured by the release of IL-8 from cells. In one specific, non-limiting example, IL-8 release is measured by indirect ELISA (enzyme-linked immunosorbent assay).

In a further embodiment, modification of an immune response includes increasing lymphocyte chemotaxis. Thus, the administration of a modified defensin, such as a modified alpha defensin, modulates T cell chemotaxis. T cell chemotaxis can be measured by any means known to one of skill in the art, but is generally measured by measuring the length of migration of the T cells, the number of migrating T cells, or both. In one specific, non-limiting example, T cell migration is measured in vitro, such as by measuring T cell migration from one cell culture chamber to another cell culture chamber through a porous membrane.

In another embodiment, modification of the immune response includes altering an inflammatory response. An inflammatory response can be measured by any means known to one of skill in the art. In one embodiment, an inflammatory response is measured by assessing the number of activated T cells present in the sample. In another embodiment, an inflammatory response is measured by a change in cytokine production, such as a change in IL-8 production. In several embodiments, increased cytokine production is a 100%, 200%, or 300% increase in cytokine production in the presence of a modified defensin.

The subject can be any mammal. In one embodiment, the subject is a human. In other embodiments, the subject may be a monkey, a rabbit, a rat, a pig, a sheep, a dog, a cat, or a mouse. In one embodiment, the subject has a disease, such as a pulmonary disease. Specific, non-limiting examples of pulmonary diseases are emphysema, adult respiratory distress syndrome, asthma, bronchopulmonary dysplasia, chronic bronchitis, sarcoidosis, pulmonary fibrosis, or cystic fibrosis. In another embodiment, the subject is infected with a pathogen, such as a bacteria, fungus, or virus. Specific, non-limiting examples of bacterial infections affecting the lungs are pneumonia, or tuberculosis.

In another embodiment, the subject has a tumor, such as a benign or a malignant tumor. Specific, non-limiting examples are lung, intestine, colon, breast, ovarian, uterine, prostate, testicular, or liver tumors.

In another embodiment, the subject has an intestinal disease. Specific, non-limiting examples of intestinal diseases are Inflammatory Bowel Diseases such as Crohn's Disease and Ulcerative Colitis.

In yet another embodiment, the subject is immunodeficient. In one specific, non-limiting example, the subject is infected with an immunodeficiency virus, such as a human immunodeficiency virus (e.g., HIV-1 or HIV-2). In a further embodiment, the subject has an autoimmune disorder.

Additional Methods

A method is disclosed herein for inhibiting the cytotoxic activity of a non-ADP-ribosylated alpha defensin polypeptide in a subject. The method includes administering to a subject a therapeutically effective amount of an ADP-ribosylated defensin polypeptide or a ribosylated defensin polypeptide to inhibit the cytotoxic activity of a non-ADP-ribosylated alpha defensin polypeptide. In one embodiment, the ADP-ribosylated defensin polypeptide or ribosylated defensin polypeptide is an alpha defensin polypeptide. In another specific, non-limiting example, the alpha defensin polypeptide is HNP-1. In a specific embodiment, an arginine residue at position 14 of the HNP-1 sequence as in SEQ ID NO:2 is ADP-ribosylated.

In one embodiment, the cytotoxic activity is measured by the ability of an alpha defensin polypeptide to lyse a cell. In several embodiments, the lysed cell is a normal cell, a malignant cell, or a cell that is resistant to host defense mechanisms.

In one embodiment, cell lysis is measured by the number of viable cells remaining in a sample containing ADP-ribosylated alpha defensin following an incubation period, compared to a control sample with the same starting number of cells but that contains non-ADP-ribosylated alpha defensin.

A method is provided herein for screening for an agent that affects ADP-ribosylation of a defensin polypeptide. The method includes exposure of a cell that expresses an adenosine-diphosphate ribosyltransferase with the agent in the presence of the defensin, and evaluating the ADP-ribosylation or ribosylation of the alpha defensin (Zolkiewska and Moss *J Biol Chem;* 34: 25273-25276, 1993).

In one embodiment, ADP-ribosylation or ribosylation is increased as compared to a control. In another embodiment, ADP-ribosylation or ribosylation is decreased as compared to a control. Suitable controls include, but are not limited to, a standard curve, a known amount of ADP-ribosylated defensin polypeptide, or a known amount of ribosylated defensin polypeptide. A suitable control also includes, but is not limited to, a cell not contacted with the agent, or a cell that does not express the adenosine-diphosphate ribosyltransferase.

To assess the ability of an agent to inhibit or alter ADP-ribosylation or ribosylation of a defensin, a series of assays can be carried out in the presence of varying concentrations of the putative modulatory compound (including zero concentration), and the extent of ADP-ribosylation or ribosylation of the defensin is determined for each assay.

Suitable agents for screening include, but are not limited to small molecules, peptides, antibodies, chemical compounds, antisense nucleic acids, or peptidomimetics. The test compound may also be a combinatorial library for screening multiple compounds. In addition, compounds identified in the method of the invention can be further evaluated, detected, cloned, sequenced, and the like, either in solution or after binding to a solid support, by any method usually applied to the detection of a specific DNA sequence, such as PCR, oligomer restriction (Saiki et al., *Bio/Technology* 3:1008-1012, 1985), allele-specific oligonucleotide (ASO) probe analysis (Conner et al., *Proc. Natl. Acad. Sci. USA* 80:278, 1983), oligonucleotide ligation assays (OLAs) (Landegren et al., *Science* 241:1077, 1988), and the like. Molecular techniques for DNA analysis have been reviewed (Landegren et al., *Science* 242:229-237, 1988).

The invention is illustrated by the following non-limiting Examples.

EXAMPLES

Example 1

Cloning, Expression and Purification of Recombinant ART-1 with a FLAG Tag

Wild-type adenosine-diphosphate ribosyltransferase (ART)-1 was cloned from a rabbit muscle cDNA library by polymerase chain reaction using forward (5'-ACGTA-CAAGCTTAGCCACCTG GTGACACGTCGAGAC, SEQ ID NO:11) and reverse (5'-ACGTACGGTACCGTCCAG-GTGGC AGGGCCTAGACTT, SEQ ID NO:12) primers. PCR products were digested with Hind III and Kpn I (Roche Molecular Biochemicals, Indianapolis, Ind.), and then subcloned into a pFLAG-MAC (Sigma, St. Louis, Mo.) expression vector that was used to transform *E. coli* ampicillin resistant BL-21 (DE 3) competent cells (Novagen Inc, Madison, Wis.). Single colonies were grown in Luria Bertani (LB) medium with ampicillin (50 µg/ml) to a change in optical density of 0.4, at 600 nm, before adding isopropyl-D thiogalactoside (IPTG) (final concentration, 0.5 mM). Following incubation for 2 hours at 30° C., bacteria were pelleted by centrifugation (15 minutes at 3,200×g, 4° C.), resuspended in 50 mM Tris (pH 8.0), 5 mM EDTA, lysozyme (0.25 mg/ml), 1.5 M NaCl, 0.1 M MgCl$_2$, DNase I (0.02 µg/ml) and protease inhibitor cocktail (Boheringer Mannheim, Mannheim Germany) (50 µg/ml), sonicated and centrifuged (45 minutes at 12,500×g, 4° C.). Supernatants were applied to anti-FLAG M2 affinity gel (Sigma) and eluted following the manufacturer's instructions. Eluates were concentrated by centrifugation at 4300×g (4° C.) using Centricon 10 columns (Millipore, Bedford, Mass.).

Example 2

ADP-Ribosyltransferase Assay

The ADP-ribosyltransferase activity of ART-1 was assayed as described (Weng et al., *J. Biol. Chem.* 274:31797-31803, 1999; Okazaki et al., *Blood.* 88:915-21, 1996). The reaction was carried out in 0.3 ml of 50 mmol/l potassium phosphate, pH 7.5, with 20 mmol/l agmatine and 0.1 mmol/l NAD, [adenine-U-$^{14}$C] NAD (281 mCi/mmol). After incubation at 30° C., samples (0.1 ml) were applied to a 1 ml column of Dowex AG 1-X2 (Biorad, Hercules, Calif.). [$^{14}$C]ADP-ribosylagmatine was eluted with 5 ml of water for radioassay.

For HNP modification by ART-1, 2 µg of synthetic HNP-1 (Bachem, Torrance, Calif.) was incubated in 200 µl of 50 mM potassium phosphate, pH 7.5, with ART-1 (24 pmol/minute/mg) and 3 mM NAD$^+$. After overnight incubation at 30° C., the mixture was solubilized in 6 M guanidine and applied to a Vydac C18 column (Nest Group, Southboro, Mass.) equilibrated with solution A (HPLC grade water, 0.1% trifluoroacetic acid). ADP-ribose-HNP-1 was separated from the unmodified form by gradient elution with solution B (100% isopropanol, 0.2% trifluoroacetic acid) at a flow rate of 1 ml/minute: 100% solution A, 0-20 minutes, 0-60% linear gradient of solution B from 20 to 80 minutes, and 95% solution B from 60 to 85 minutes (FIG. 1). Fractions were analyzed by MALDI mass spectrometry as described (Rivera-Nieves et al., *J Biol. Chem.* 274:19525-19531, 1999).

Peptides with a mass of 3,441 daltons (retention time 48.5 minutes), consistent with HNP-1 (calculated mass equivalent to 3,442 daltons), and peptides with a mass of 3,983 daltons (retention time 46.5 minutes), consistent with mono-ADP-ribosyl-HNP (calculated mass equivalent to 3,983 daltons), were identified. Modified HNP exhibited an absorbance peak at 258 nm, which was not exhibited by HNP (FIG. 1D, inset). The ADP-ribose was released from modified HNP by incubating the HNP with ADP-ribosylarginine hydrolase, yielding the unmodified defensin.

For ADP-ribosylation of intact cells, intact C2C12 or G8 cells attached to culture plates were incubated for 1 hour at 37° C. in PBS (2 ml for a 100 mm plate, 1 ml for a 60 mm plate), 5 mM [adenylate—$^{32}$P]NAD (4 Ci/mmol) and 1 mM ADP-ribose, washed twice with PBS, lysed with 0.5 ml of lysis buffer (3% SDS, 0.1 M sodium acetate (pH 6.8), 5 mM EDTA), scraped and boiled for 10 minutes. Protein concentration was determined for the cells harvested from each plate. For SDS-PAGE analysis, 100 µg of protein was precipitated with 10% trichloroacetic acid, suspended in gel-loading buffer and subjected to SDS-PAGE on 8% gel. Gels were stained for protein, dried and exposed to Kodak-X-Omat film for 24 hours at −80° C. with an intensifying screen. The time-course of labeling of a 97 kilodalton protein was measured using a ProsphorImager (Molecular Dynamics) (Zolkiewska and Moss, *J. Biol. Chem.* 34: 25273-25276, 1993).

Example 3

Electrospray Mass Spectrometric Analysis of ADP-Ribosylated HNP-1

To identify the modified amino acid in HNP-1, reduced ADP-ribosylated HNP-1 was digested with trypsin and the fragments were analyzed by mass spectrometry. Samples (2 µg) of ADP-ribosyl-HNP-1 and HNP-1 were reduced by incubation in 50 of 100 mM Tris-HCl (pH 8), 1 mM EDTA, and 20 mM dithiothrietol for 1 hour at 37° C. before incubation for 6 hours at 37° C. with trypsin (1 µg) (Sigma) in 100 mM, $NH_4HCO_3$ (total volume, 100 µl). The modified site was identified by electrospray mass spectrometry as described (Rivera-Nieves et al., *J. Biol. Chem.* 274:19525-19531, 1999).

A peak representing a peptide with a mass of 1,626.3 daltons, compatible with ADP-ribosylated fragment $P_{6-15}$ (calculated mass equivalent to 1,626.3 daltons), was observed. This peak, unique to ADP-ribosylated HNP-1, was generated by the inhibition of trypsin cleavage of the defensin peptide as a result of ADP-ribosylation at arginine 14. Spectral analysis was consistent with the presence of adenosine in the peptide.

Example 4

Cytotoxicity Assay

Figure 2:
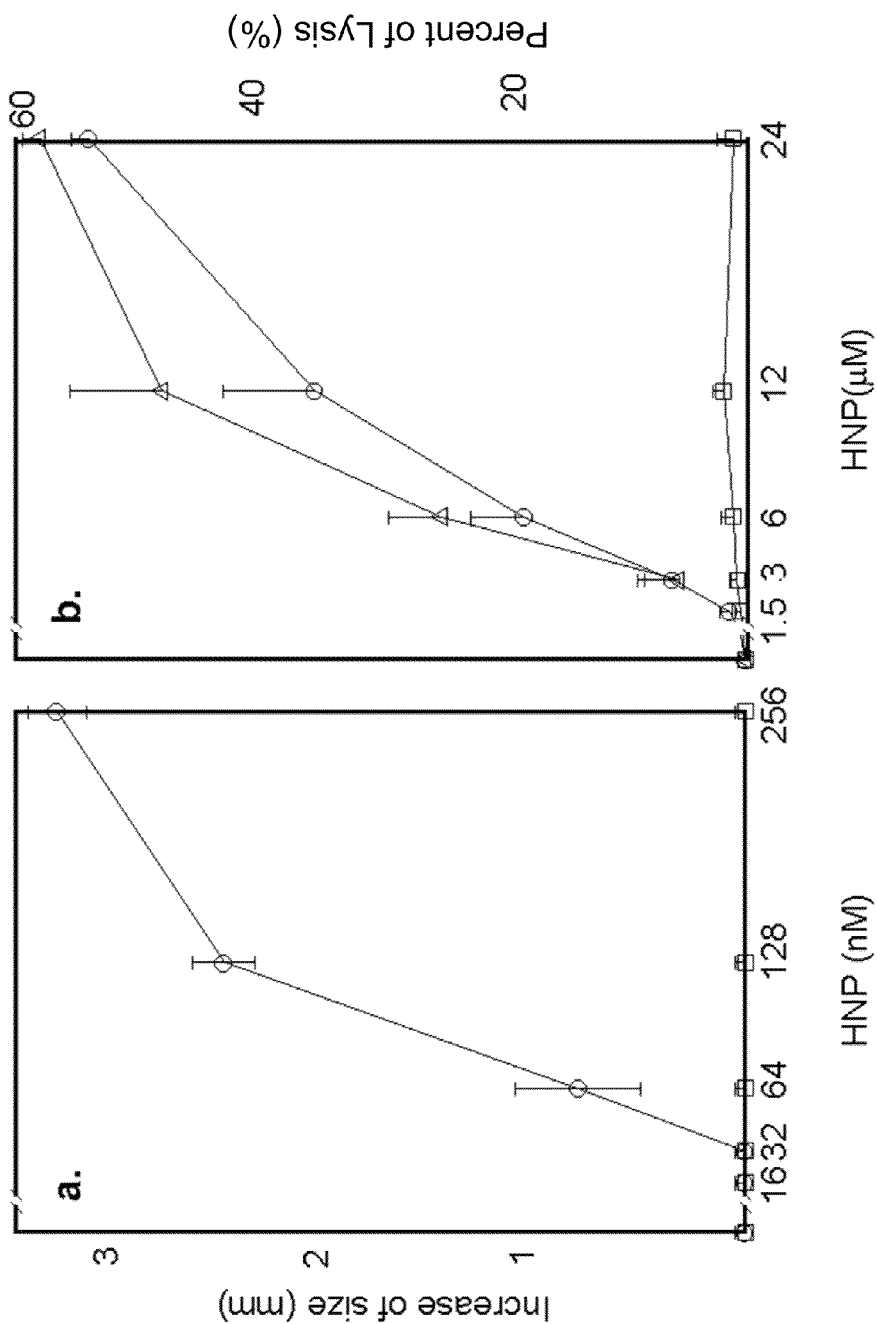
FIG. 2 is a series of dose curves that demonstrate the antimicrobial and cytotoxic activities of ADP-ribosylated HNP-1 and non-ADP-ribosylated HNP-1.

The antibacterial activity of various concentrations of HNP-1 and ADP-ribosyl-HNP-1 (16 nM, 32 nM, 64 nM, 128 nM, 256 nM) on *Escherichia coli* ATCC43827 (American Type Culture Collection, Rockville, Md.) was evaluated by the radial diffusion assay (Takemura et al., *Antimicrob. Agents Chemother.* 40: 2280-2284, 1996). Antimicrobial activity was positively correlated with the diameter of a zone cleared of *E. coli* growth (minus the diameter of the central well (3 mm)). The results (FIG. 2A) indicate that ADP-ribosylated HNP-1 had a reduced antibacterial activity, compared to unmodified HNP-1, for *E. coli* ATCC43827, as measured by the radial diffusion assay.

Example 5

Chromium Release Assay

Chromium ($^{51}$Cr)-labeled A549 cells (American Type Culture Collection) were incubated (18 hours, 37° C.) in 100 µl of serum-free RPMI (Gibco Fluids Inc., Rockville, Md.) containing various concentrations of HNP-1, synthetic HNP-1, or ADP-ribosyl-HNP-1 (1.5 µM, 3 µM, 6 µM, 12 µM, 24 µM) to quantify defensin cytotoxicity. Cytotoxicity was positively correlated with the amount of chromium released from lysed cells (Panyutich et al., *Am. J. Respir. Cell. Mol. Biol.* 12:351-357, 1995). Percent of lysis was calculated as $(cpm_{exp}-cpm_{spont})/(cpm_{max}-cpm_{spont})\times100$ (exp, experimental conditions; max, maximal release; spont, spontaneous release). The results (FIG. 2B) indicate that ADP-ribosylated HNP-1 was less cytotoxic than unmodified HNP-1 for A549 cells.

Example 6

Radial Diffusion and Chromium Release Assays to Measure the Effect of ADP-Ribosylated HNP-1 on HNP-1 Cytotoxic Activity HNP-1 (100 nM) was incubated for 1 hour at 37° C. with various concentrations of ADP-ribosylated HNP-1 (0-800 nM) before the initiation of the *E. coli* radial diffusion assay. The radial diffusion assay was performed as described in Example 4.

HNP-1 (12 µM) was incubated with various concentrations of ADP-ribosyl-HNP-1 (0-12 µM) for 1 hour at 37° C. before the initiation of the chromium release assay. The chromium release assay was performed as described in Example 5. HNP-1 and ADP-ribosyl-HNP-1 (0-12 µM) were included as controls.

Figure 3:
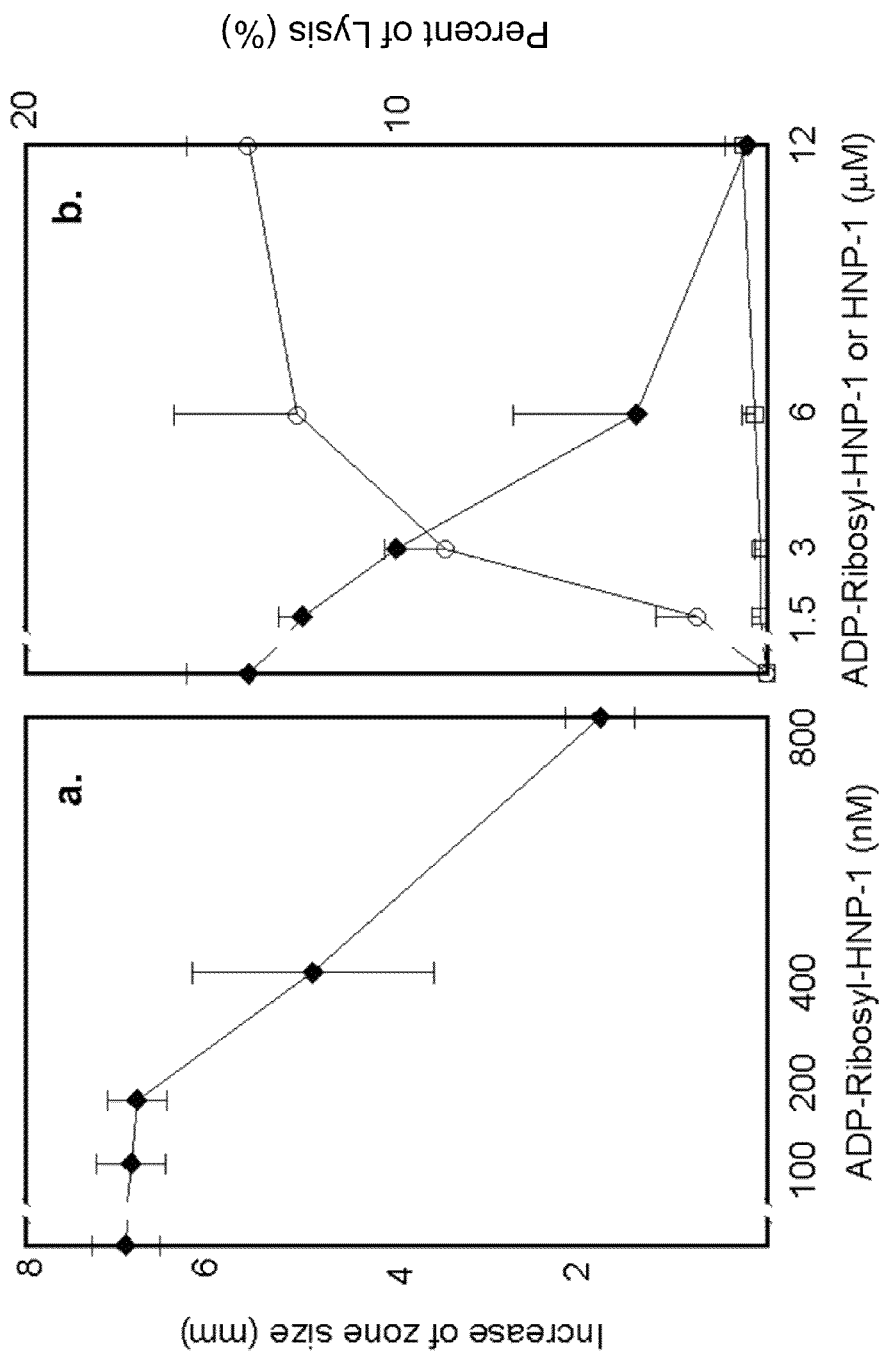
FIG. 3 is a series of dose curves that demonstrate the effects of ADP-ribosylated-HNP-1 on HNP-1 antimicrobial and cytotoxic activity.

The radial diffusion and chromium release assays demonstrated that ADP-ribosylated HNP-1 blocked the cytotoxic activity of HNP-1 in a concentration-dependent manner (FIG. 3). Another experiment, using a higher HNP-1 concentrations (24 µM), showed similar results.

Example 7

IL-8 Production by A549 Cells

A549 cells ($3\times10^4$ cells per well) were incubated in a 96-well plate in 200 µl of serum-free RPMI medium (Gibco Fluids Inc) containing ADP-ribosyl-HNP-1 or HNP-1 (0.25, 0.75, 1.5, 3 µM). Culture medium was sampled after 12 or 24 hours of incubation and IL-8 content in the medium was assayed by indirect ELISA (FIGS. 4A and 4B) according to the manufacturer's instructions (R & D System Inc. Minneapolis, Minn.). At concentrations of 0.75 and 1.5 µM, IL-8 release into the medium was significantly higher with ADP-ribosylated HNP-1 than with the unmodified peptide (P=0.01). At a higher peptide concentration, 3 µM, no differences were observed.

Example 8

Chemotaxis Assay

CD3$^+$ T-cells were isolated from human peripheral blood prepared by leukapheresis (NIH, Department of Transfusion Medicine, Bethesda, Md.) (Chertov et al, *J. Biol. Chem.* 271: 2935-2940, 1996) and suspended in migration medium (RPMI 1640, 0.5% bovine serum albumin, 25 mM HEPES).

Figure 4:
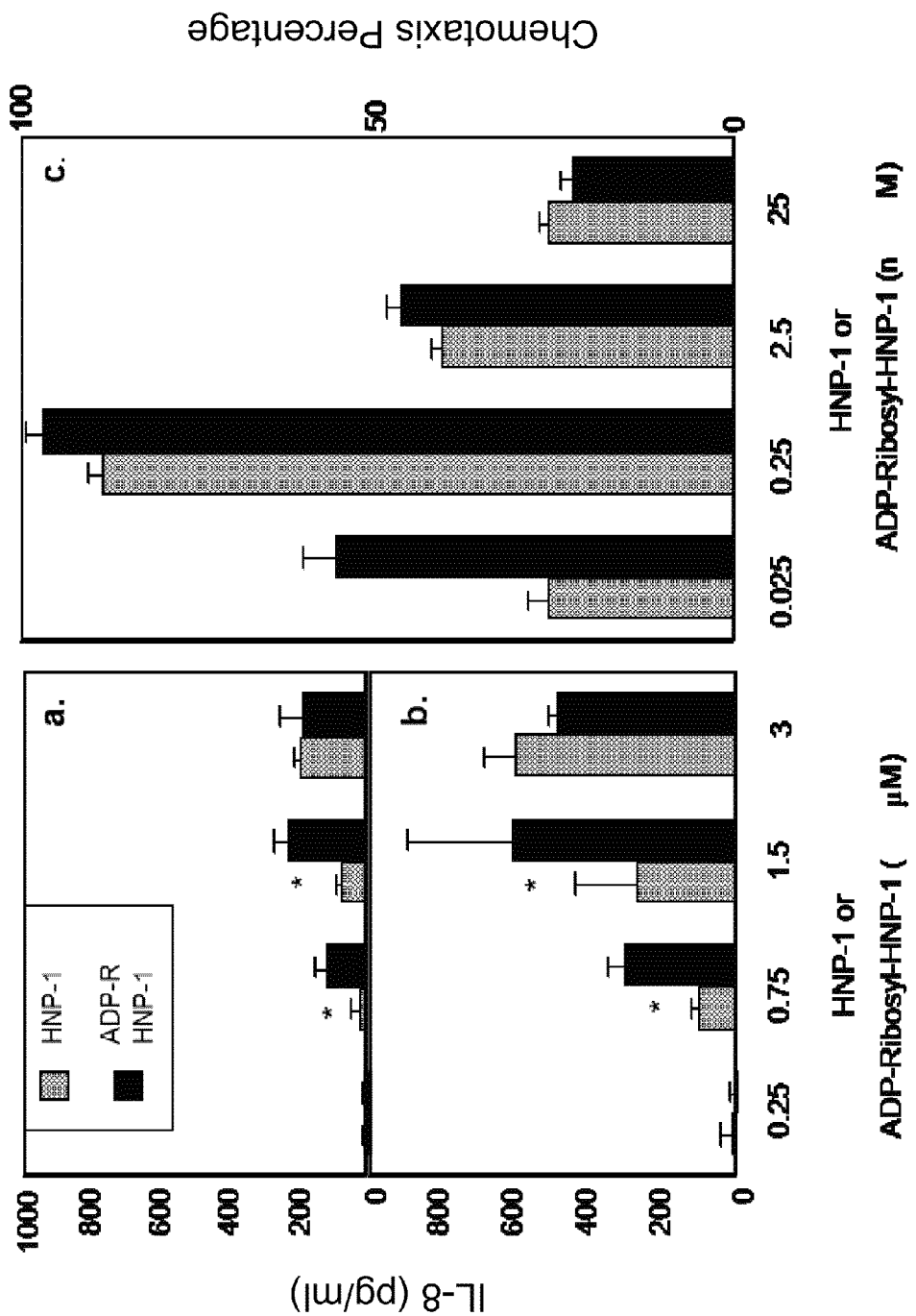
FIG. 4 is a series of bar graphs that demonstrate the effects of ADP-ribosylated HNP-1 and HNP-1 on interleukin (IL)-8 release by A549 cells and on T cell chemotaxis. Cells were incubated for 12 hours (FIG. 4A) or 24 hours (FIG. 4B) with the indicated concentrations of HNP-1 or ADP-ribosylated HNP-1 before analysis of the media. The IL-8 present in the medium of the cells incubated without defensins has been subtracted. Data are means±½ range of 2 separate experiments, each performed in triplicate. *$P<0.05$ for the difference in IL-8 release by HNP-1 and ADP-R HNP-1.

Inserts coated with collagen IV (Becton Dickinson Labware, Bedford, Mass.) were placed into 24-well culture plates to form upper and a lower chambers in each well. Upper chambers were wetted with migration medium, then 500 µl of migration medium with or without ADP-ribosyl-HNP-1 or HNP-1 (0.025 to 25 nM) were added to the lower chamber. Cells were added to the upper chamber and plates were incubated at 37° C. in 5% $CO_2$ for 4 hours. Cells incubated in the presence or absence of (macrophage inflammatory protein-1β) MIP-1β (5 ng/ml) were the positive and negative controls, respectively. Lymphocytes that had migrated to the lower chamber were harvested by centrifugation and counted in a hematocytometer. Chemotaxis percentage was calculated as follows: (number of cells migrated to the lower chamber in the experimental conditions−number of cells migrated in the negative control)/(number of cells migrated in the positive control−number of cells migrated in negative control)×100. The results indicated that ADP-ribosyl HNP-1 retained the ability to recruit T cells at a level that was comparable to unmodified HNP (FIG. 4C).

Example 9

Isolation of ADP-Ribosylated HNP-1 from Bronchoalveolar Lavage

To identify ADP-ribosyl HNP-1 in humans, bronchoalveolar lavage (BAL) was performed on 18 smokers and 10 non-smokers, none of whom had signs of pulmonary infection. Characteristics of the smokers are summarized in Table 1, below. The two populations did not differ significantly in age, gender, or pulmonary function. Samples (10 ml) of BAL from 18 cigarette smokers (NHLBI IRB protocol #95-H-167) and 10 healthy non-smokers were applied to SepPack C-18 cartridges (Waters, Milford, Mass.) equilibrated in 10% isopropanol/0.1% trifluoroacetic acid (TFA), washed with the same buffer, and eluted with 50% isopropanol/0.1% TFA. The eluted proteins were concentrated in 6 M guanidine/0.1% acetic acid and separated on a Vydac column C18 HPLC column. Absorbence peaks (210 nm) corresponding to the retention times of HNP-1 and ADP-ribosylated HNP-1 were analyzed by Matrix Assisted Laser Desorption Ionization-Time of Flight-Mass Spectrometry (MALDI-MS). Molecules with masses corresponding to ADP-ribosylated HNP-1 were further characterized. ADP-ribosylated HNP-1 (0.2 µg) was incubated in 200 µl of 250 mM $NaHCO_3$, 25 mM $MgCl_2$, alkaline phosphatase (5 µg) and pyrophosphatase (5 µg) (Sigma), for 30 minutes at 37° C., before termination of the reaction with 6 M guanidine, separation of reaction products by RP-HPLC and analysis by MALDI-MS. ADP-ribosylated HNP-1 (0.42 µg) was incubated overnight at 37° C. with recombinant human ADP-ribosylarginine hydrolase (1 µg) in 100 µl of 50 mM Tris (pH 7.5), 5 mM dithiothrietol, 10 mM $MgCl_2$ (Moss et al. *Proc. Natl. Acad. Sci.* 82: 5603-5607, 1985), followed by desalting and concentration using Zip-$Tip_{C18}$ (Millipore), and analysis by MALDI-MS.

Figure 5:
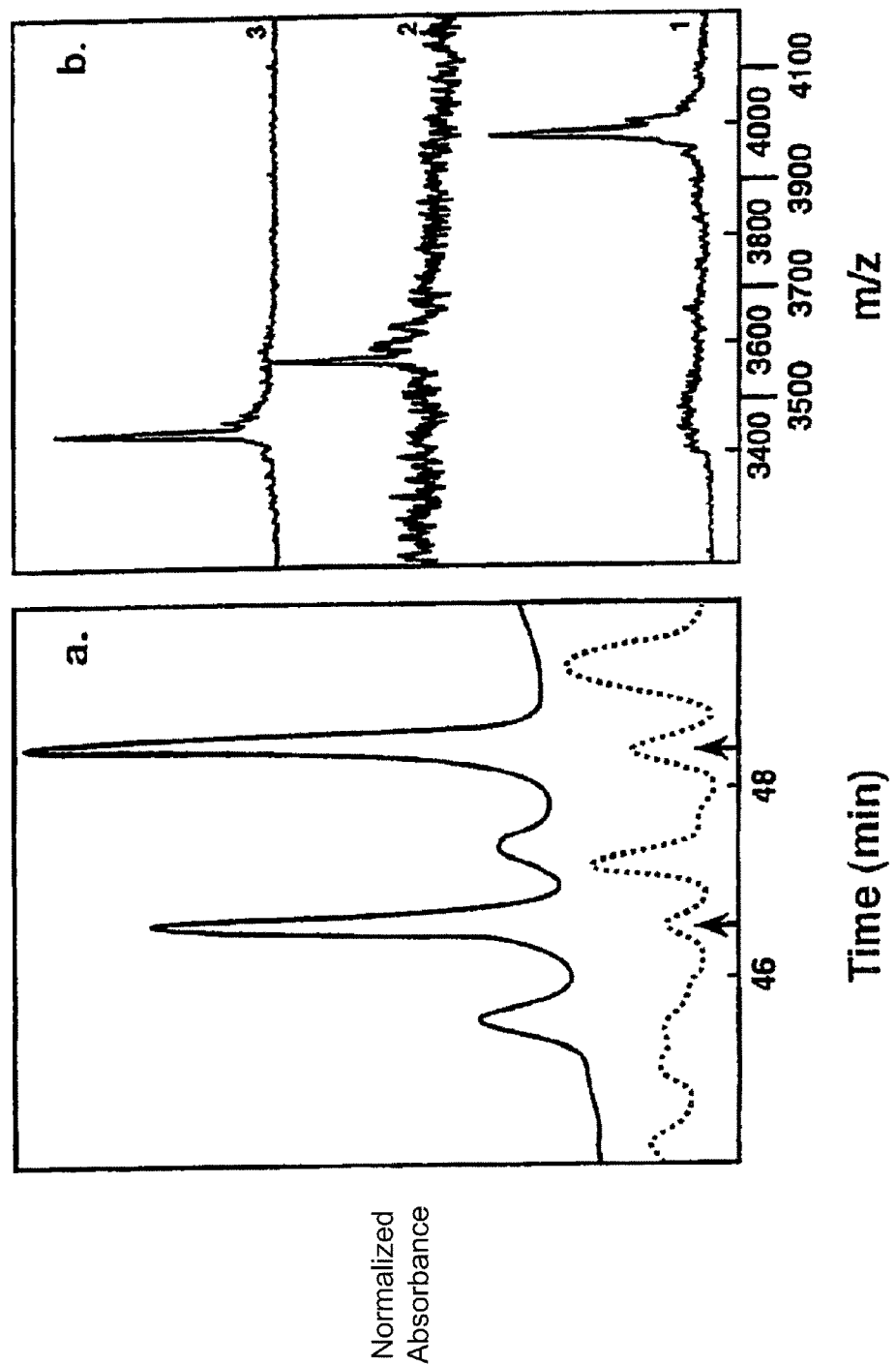
FIG. 5 is a series of elution profiles that characterize the ADP-ribosylated defensins obtained from bronchoalveolar lavage fluid.
Figure 6:
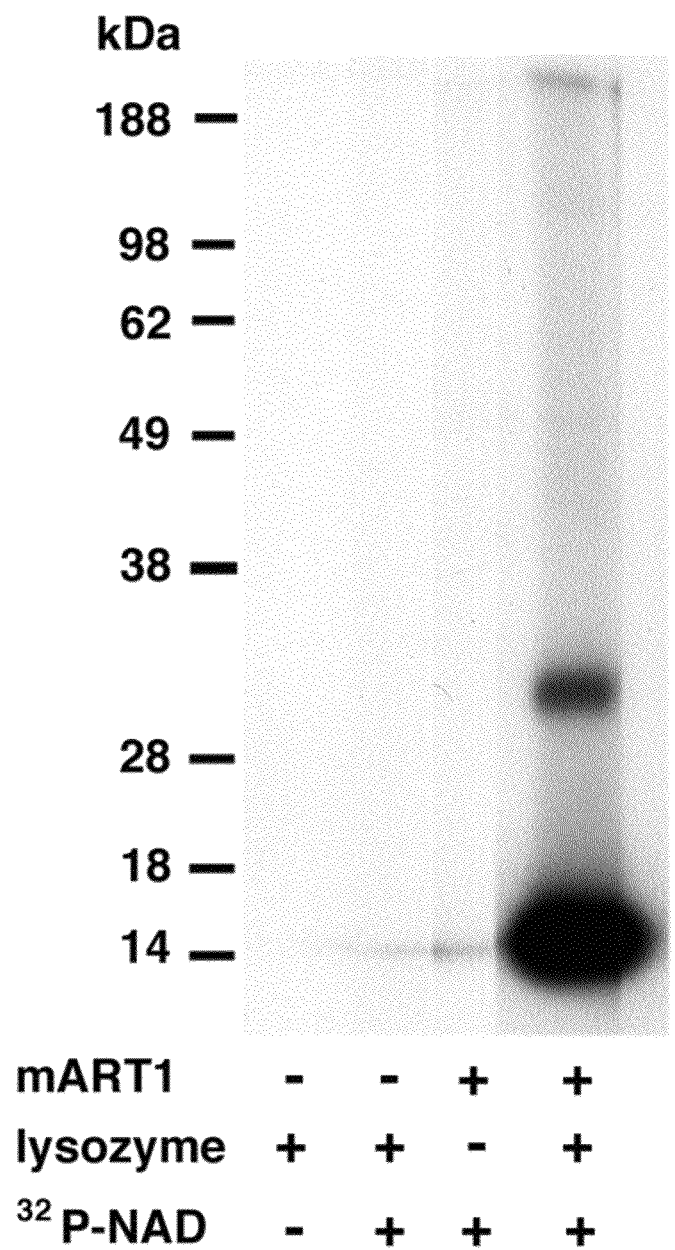
FIG. 6 is a digital image of an autoradiogram. The lane corresponding to the [$^{32}$P]NAD reaction mixture containing both ART-1 and 5 µg of lysozyme reveals a strong band at approximately 14 kDa, consistent with [$^{32}$P]ADP-ribosylation of lysozyme.

BAL findings are summarized in Table 1, below. The total number of cells recovered from BAL of smokers was 4-fold that recovered from controls (P<0.001), with a greater absolute number of neutrophils in the BAL fluid samples of smokers. RP-HPLC analysis of BAL fluid samples from 18 smokers revealed peaks with the same elution time as authentic HNP in 12 of the samples; four of these twelve samples showed peaks with elution times identical to that of ADP-ribosylated HNP-1 (FIG. 5A). MALDI mass spectral (MS) analysis demonstrated a molecule with a mass of 3,983 daltons, confirming the presence of ADP-ribosylated HNP-1 (calculated mass equivalent to 3,983 daltons) (FIG. 5B-1). Defensins were not detected in BAL fluids from the non-smoker group.

The ADP-ribosylated HNP-1 was further characterized by incubating it with pyrophosphatase/phosphatase to remove the ADP moiety, producing ribosyl-HNP, or with ADP-ribosylarginine hydrolase, which cleaves the ribose-arginine linkage, releasing HNP. After incubation with pyrophosphatase and alkaline phosphatase, MALDI analysis of the peak separated by RP-HPLC separation, showed a molecule of 3,575 daltons, consistent with ribosyl-HNP-1, produced by removal of ADP from the ADP-ribose-HNP-1 (FIG. 5B-2) (calculated mass equivalent to 3,574 daltons). The site of linkage of ADP-ribose to HNP was confirmed after incubation with ADP-ribosylarginine hydrolase, which released a molecule of 3,444 daltons consistent with HNP-1 (calculated 3,443 daltons) (FIG. 5B-3).

TABLE 1

Characteristics of smokers and bronchoalveolar lavage fluid samples

| | Population | | BronchoAlveolar Lavage | | | |
|---|---|---|---|---|---|---|
| Number | Smoking History[A] | FV-1%[B] | Total Cells[C] | PMN[D] | HNP-1 | ADP-R HNP-1 |
| 1 | 40/d 30 yrs | 138 | 245 | 2.1 | + | + |
| 2 | 30/d 11 yrs | 73 | 126 | 1.8 | + | − |
| 3 | 40/d 5 yrs | 93 | 140 | 1.6 | − | − |
| 4 | 10/d 37 yrs | 113 | 55 | 1 | + | − |
| 5 | 40/d 12 yrs | 110 | 95 | 1 | − | − |
| 6 | 20/d 29 yrs | 109 | 103 | 1.9 | − | − |
| 7 | 20/d 25 yrs | 126 | 166 | 3 | + | + |
| 8 | 20/d 15 yrs | 95 | 108 | 3.5 | + | − |
| 9 | 20/d 20 yrs | 96 | 169 | 2 | + | − |
| 10 | 10/d 9 yrs | 143 | 46 | 3 | − | − |
| 11 | 40/d 16 yrs | 115 | 150 | 0.5 | + | − |
| 12 | 20/d 36 yrs | 130 | 140 | 1.3 | − | − |
| 13 | 30/d 15 yrs | 80 | 280 | 8 | + | − |
| 14 | 20/d 30 yrs | 96 | 135 | 0.8 | + | − |
| 15 | 20/d 10 yrs | 109 | 105 | 1 | + | − |
| 16 | 30/d 26 yrs | 97 | 119 | 0.5 | + | + |
| 17 | 30/d 30 yrs | 66 | 44 | 0.5 | + | + |
| 18 | 15/d 15 yrs | 103 | 52 | 0.5 | − | − |

[A]cigarette per day, duration
[B]percent of predicted FV-1 (FV-1, Forced Expiratory Volume in 1 second)
[C]total cells × $10^6$
[D]percent of total cells Example 10

ADP-Ribosylation of Lysozyme by ART-1

ART-1 was collected from NMU (rat mammary carcinoma) cells, transfected with mouse ART-1 cDNA inserted in a pMAMneo plasmid. Protein expression was induced in the NMU cells with 1 mM dexamethazone for 24 hours. Cells were then incubated with phosphatidylinositol-specific phospholipase C (PIPLC) (0.05 units per 300 µl Dulbeccos's phosphate buffered saline) for 1 hour at 37° C., sedimented by centrifugation and the supernatant containing ART-1 proteins was collected.

Lysozyme (5 µg, obtained from chicken egg white; Sigma, St Louis, Mo.) was incubated with mouse ADP-ribosyltransferase 1 (ART-1) in a reaction mix containing 50 mM potassium phosphate pH 7.5, 1 mM adenosine diphosphate ribose, 10 µM [$^{32}$P]NAD (10 µCi per assay reaction) for 1 hour at 30° C. After TCA precipitation (10% final concentration), proteins were separated by SDS PAGE using a 12% acrylamide gel. The gel was stained with Coomassie blue protein dye and exposed to X-ray film (Kodak XAR) for 5 hours. The resulting autoradiogram revealed a strong radioactive band, at approximately 14 kDa (molecular weight of lysozyme is approximately 14 kDa) in the lane corresponding to the [$^{32}$P] NAD reaction mixture containing both ART-1 and 5 μg of lysozyme. The lanes containing lysozyme, either with or without the [$^{32}$P]NAD reaction mix, were blank. Thus, the results indicate that ART-1 can ADP-ribosylate lysozyme.

This disclosure provides modified antimicrobial agents, such as modified defensin polypeptides. The disclosure further provides method of modulating an immune response using these modified polypeptides. It will be apparent that the precise details of the methods described may be varied or modified without departing from the spirit of the described invention. We claim all such modifications and variations that fall within the scope and spirit of the claims below.

We claim:

1. A method of inhibiting a cytotoxic activity of a non-ADP-ribosylated or a non-ribosylated alpha defensin polypeptide comprising an amino acid sequence at least 90% identical to any one of SEQ ID NOs: 2, 3, or 4, comprising in vitro contacting the non-ADP-ribosylated or the non-ribosylated alpha defensin polypeptide with an ADP-ribosylated or a ribosylated alpha defensin polypeptide comprising an amino acid sequence at least 90% identical to any one of SEQ ID NOs: 2, 3, or 4, thereby inhibiting the cytotoxic activity of the non-ADP-ribosylated or non-ribosylated alpha defensin polypeptide.

2. The method of claim 1, wherein the non-ADP-ribosylated or non-ribosylated alpha defensin polypeptide and/or the ADP-ribosylated or ribosylated alpha defensin polypeptide comprises an amino acid sequence at least 95% identical to any one of SEQ ID NOs: 2, 3, or 4.

3. The method of claim 2, wherein the non-ADP-ribosylated or non-ribosylated alpha defensin polypeptide and/or the ADP-ribosylated or ribosylated alpha defensin polypeptide comprises the amino acid sequence set forth as SEQ ID NO: 2, 3, or 4.

4. The method of claim 3, wherein the non-ADP-ribosylated or non-ribosylated alpha defensin polypeptide and/or the ADP-ribosylated or ribosylated alpha defensin polypeptide consists of the amino acid sequence set forth as SEQ ID NO: 2, 3, or 4.

5. A method of inhibiting a cytotoxic activity of a non-ADP-ribosylated or a non-ribosylated alpha defensin polypeptide comprising an amino acid sequence at least 90% identical to any one of SEQ ID NOs: 2, 3, or 4, comprising administering to a subject having an inflammatory pulmonary disease a therapeutically effective amount of the an ADP-ribosylated or a ribosylated alpha defensin polypeptide comprising an amino acid sequence at least 90% identical to any one of SEQ ID NOs: 2, 3, or 4.

6. The method of claim 5, wherein the subject is a human.

7. The method of claim 5, wherein the inflammatory pulmonary disease is cystic fibrosis, emphysema, asthma, sarcoidosis, chronic bronchitis, pulmonary fibrosis, pneumonia, or adult respiratory distress syndrome.

8. The method of claim 5, wherein the non-ADP-ribosylated or non-ribosylated alpha defensin polypeptide and/or the ADP-ribosylated or ribosylated alpha defensin polypeptide comprises an amino acid sequence at least 95% identical to any one of SEQ ID NOs: 2, 3, or 4.

9. The method of claim 8, wherein the non-ADP-ribosylated or non-ribosylated alpha defensin polypeptide and/or the ADP-ribosylated or ribosylated alpha defensin polypeptide comprises the amino acid sequence set forth as SEQ ID NO: 2, 3, or 4.

10. The method of claim 9, wherein the non-ADP-ribosylated or non-ribosylated alpha defensin polypeptide and/or the ADP-ribosylated or ribosylated alpha defensin polypeptide consists of the amino acid sequence set forth as SEQ ID NO: 2, 3, or 4.

* * * * *